(12) United States Patent
Maihle et al.

(10) Patent No.: US 7,390,632 B2
(45) Date of Patent: Jun. 24, 2008

(54) SOLUBLE ERBB3 RECEPTOR ISOFORMS

(75) Inventors: Nita J. Maihle, Rochester, MN (US); Hakjoo Lee, Rochester, MN (US)

(73) Assignee: Tumor Biology Investment Group, Inc., Lexington, KY (US)

(*) Notice: Subject to any disclaimer, the term of this patent is extended or adjusted under 35 U.S.C. 154(b) by 0 days.

(21) Appl. No.: 10/159,353

(22) Filed: May 31, 2002

(65) Prior Publication Data

US 2003/0190702 A1 Oct. 9, 2003

Related U.S. Application Data

(60) Provisional application No. 60/294,824, filed on May 31, 2001.

(51) Int. Cl.
*C07H 21/04* (2006.01)
*C12N 15/00* (2006.01)
*C12N 5/00* (2006.01)

(52) U.S. Cl. .................. 435/7.92; 536/23.1; 435/320.1; 435/325

(58) Field of Classification Search ................ 435/69.1, 435/320.1, 325; 530/350
See application file for complete search history.

(56) References Cited

U.S. PATENT DOCUMENTS 5,183,884 A * 2/1993 Kraus et al. ................ 536/23.5

OTHER PUBLICATIONS

Chen et al., J Biol Chem. Mar. 29, 1996; 271(13):7620-7629.*
Tzahar et al., J Biol Chem. Oct. 7, 1994; 269((40):25226-25233.*
Sliwkowski et al., J Biol Chem. May 20, 1994; 269(20):14661-14665.*
UniProt database entry, accession No. Q9BUD7.*
Katoh et al., Biochem and Biophys Res Comm. May 14, 1993; 192(3):1189-1197.*
Strausberg et al., PNAS USA. Dec. 24, 2002;99(26):16899-903. Epub Dec. 11, 2002.*
Plowman et al., PNAS USA 1990 87:4905-4909.*
Wells, 1990, Biochemistry 29:8509-8517.*
Bowie et al, 1990, Science 247:1306-1310.*

* cited by examiner

*Primary Examiner*—Gary B. Nickol
*Assistant Examiner*—Cherie Woodward
(74) *Attorney, Agent, or Firm*—Christy G. Rothwell, Esq.; Cohen & Grigsby, P.C.

(57) ABSTRACT

The present invention discloses a system and method using the human ErbB3 receptor, p85-sErbB3, as a negative regulator of heregulin-stimulated ErbB2, ErbB3, and ErbB4 activation. The present invention also discloses a system and method of p85-sErbB3 binding to heregulin with an affinity comparable to that of full-length ErbB3, and competitively inhibiting high affinity heregulin binding to ErbB2/3 heterodimers on the cell surface of breast carcinoma cells. The present invention also uses p85-sErbB3 to inhibit heregulin-induced phosphorylation of ErbB2, ErbB3, and ErbB4 in cells and uses p85-sErbB3 as a negative regulator of heregulin-stimulated signal transduction and as a block for cell growth. The present invention is also directed to nucleic acids and expression vectors encoding p85-sErbB3, host cells harboring such expression vectors, and methods of preparing the protein. The present invention discloses a system and method of therapeutic applications in human malignancies associated with heregulin-mediated cell growth such as breast and prostate cancer.

Figure 1:
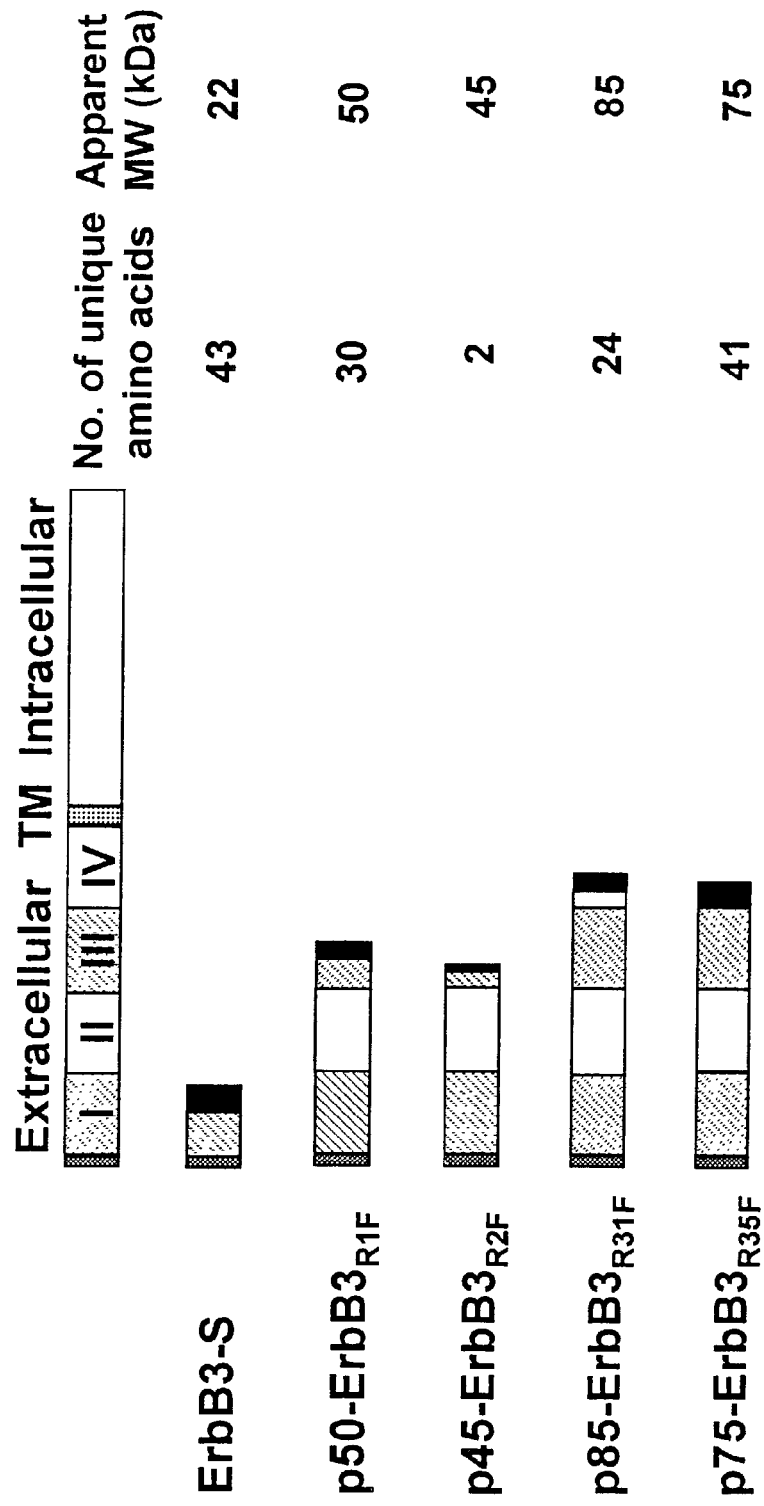

7 Claims, 24 Drawing Sheets p85-sErbB3 protein
AA 1-538: The N-terminal ErbB3 sequence
AA 1-19: signal peptide
AA 539-562: p85-sErbB3 unique sequence

```
                         10                                    20
MetArgAlaAsnAspAlaLeuGlnValLeu GlyLeuLeuPheSerLeuAlaArgGlySer>

30                                    40
GluValGlyAsnSerGlnAlaValCysPro GlyThrLeuAsnGlyLeuSerValThrGly>

50                                    60
AspAlaGluAsnGlnTyrGlnThrLeuTyr LysLeuTyrGluArgCysGluValValMet>

70                                    80
GlyAsnLeuGluIleValLeuThrGlyHis AsnAlaAspLeuSerPheLeuGlnTrpIle>

90                                   100
ArgGluValThrGlyTyrValLeuValAla MetAsnGluPheSerThrLeuProLeuPro>

110                                   120
AsnLeuArgValValArgGlyThrGlnVal TyrAspGlyLysPheAlaIlePheValMet>

130                                   140
LeuAsnTyrAsnThrAsnSerSerHisAla LeuArgGlnLeuArgLeuThrGlnLeuThr>

150                                   160
GluIleLeuSerGlyGlyValTyrIleGlu LysAsnAspLysLeuCysHisMetAspThr>

170                                   180
IleAspTrpArgAspIleValArgAspArg AspAlaGluIleValValLysAspAsnGly>

190                                   200
ArgSerCysProProCysHisGluValCys LysGlyArgCysTrpGlyProGlySerGlu>

210                                   220
AspCysGlnThrLeuThrLysThrIleCys AlaProGlnCysAsnGlyHisCysPheGly>

230                                   240
ProAsnProAsnGlnCysCysHisAspGlu CysAlaGlyGlyCysSerGlyProGlnAsp>

250                                   260
ThrAspCysPheAlaCysArgHisPheAsn AspSerGlyAlaCysValProArgCysPro>

270                                   280
GlnProLeuValTyrAsnLysLeuThrPhe GlnLeuGluProAsnProHisThrLysTyr>

290                                   300
GlnTyrGlyGlyValCysValAlaSerCys ProHisAsnPheValValAspGlnThrSer>
```

FIG.1A

```
                      310                              320
    CysValArgAlaCysProProAspLysMet  GluValAspLysAsnGlyLeuLysMetCys>
                      330                              340
    GluProCysGlyGlyLeuCysProLysAla  CysGluGlyThrGlySerGlySerArgPhe>
                      350                              360
    GlnThrValAspSerSerAsnIleAspGly  PheValAsnCysThrLysIleLeuGlyAsn>
                      370                              380
    LeuAspPheLeuIleThrGlyLeuAsnGly  AspProTrpHisLysIleProAlaLeuAsp>
                      390                              400
    ProGluLysLeuAsnValPheArgThrVal  ArgGluIleThrGlyTyrLeuAsnIleGln>
                      410                              420
    SerTrpProProHisMetHisAsnPheSer  ValPheSerAsnLeuThrThrIleGlyGly>
                      430                              440
    ArgSerLeuTyrAsnArgGlyPheSerLeu  LeuIleMetLysAsnLeuAsnValThrSer>
                      450                              460
    LeuGlyPheArgSerLeuLysGluIleSer  AlaGlyArgIleTyrIleSerAlaAsnArg>
                      470                              480
    GlnLeuCysTyrHisHisSerLeuAsnTrp  ThrLysValLeuArgGlyProThrGluGlu>
                      490                              500
    ArgLeuAspIleLysHisAsnArgProArg  ArgAspCysValAlaGluGlyLysValCys>
                      510                              520
    AspProLeuCysSerSerGlyGlyCysTrp  GlyProGlyProGlyGlnCysLeuSerCys>
                      530                              540
    ArgAsnTyrSerArgGlyGlyValCysVal  ThrHisCysAsnPheLeuAsnGlyTyrSer>
                      550                              560
    LysGlySerGlnSerArgMetGlyGlyGly  GlyAlaLeuGlnTrpAsnCysSerGlyGly>
         562
    IleGln
```

FIG.1B p85-sErbB3 cDNA sequence (R31F)
nt 1-1673: The N-terminal ErbB3 sequence
nt 1674-1761: unique to p85-sErbB3

```
          10        20        30        40        50        60
cgggccccccctcgaggtcg ggccggacttggctgggctc ccttcaccctctgcggagtc
          70        80        90       100       110       120
ATGAGGGCGAACGACGCTCT GCAGGTGCTGGGCTTGCTTT TCAGCCTGGCCCGGGGCTCC 130       140       150       160       170       180
GAGGTGGGCAACTCTCAGGC AGTGTGTCCTGGGACTCTGA ATGGCCTGAGTGTGACCGGC 190       200       210       220       230       240
GATGCTGAGAACCAATACCA GACACTGTACAAGCTCTACG AGAGGTGTGAGGTGGTGATG 250       260       270       280       290       300
GGGAACCTTGAGATTGTGCT CACGGGACACAATGCCGACC TCTCCTTCCTGCAGTGGATT 310       320       330       340       350       360
CGAGAAGTGACAGGCTATGT CCTCGTGGCCATGAATGAAT CTCTACTCTACCATTGCCC 370       380       390       400       410       420
AACCTCCGCGTGGTGCGAGG GACCCAGGTCTACGATGGGA AGTTTGCCATCTTCGTCATG 430       440       450       460       470       480
TTGAACTATAACACCAACTC CAGCCACGCTCTGCGCCAGC TCCGCTTGACTCAGCTCACC 490       500       510       520       530       540
GAGATTCTGTCAGGGGGTGT TTATATTGAGAAGAACGATA AGCTTTGTCACATGGACACA 550       560       570       580       590       600
ATTGACTGGAGGGACATCGT GAGGGACCGAGATGCTGAGA TAGTGGTGAAGGACAATGGC 610       620       630       640       650       660
AGAAGCTGTCCCCCCTGTCA TGAGGTTTGCAAGGGGCGAT GCTGGGGTCCTGGATCAGAA 670       680       690       700       710       720
GACTGCCAGACATTGACCAA GACCATCTGTGCTCCTCAGT GTAATGGTCACTGCTTTGGG 730       740       750       760       770       780
CCCAACCCCAACCAGTGCTG CCATGATGAGTGTGCCGGGG GCTGCTCAGGCCCTCAGGAC 790       800       810       820       830       840
ACAGACTGCTTTGCCTGCCG GCACTTCAATGACAGTGGAG CCTGTGTACCTCGCTGTCCA 850       860       870       880       890       900
CAGCCTCTTGTCTACAACAA GCTAACTTTCCAGCTGGAAC CCAATCCCCACACCAAGTAT 910       920       930       940       950       960
CAGTATGGAGGAGTTTGTGT AGCCAGCTGTCCCCATAACT TTGTGGTGGATCAAACATCC
```

FIG. 1C

```
     970        980        990       1000       1010       1020
TGTGTCAGGGCCTGTCCTCC TGACAAGATGGAAGTAGATA AAAATGGGCTCAAGATGTGT 1030       1040       1050       1060       1070       1080
GAGCCTTGTGGGGGACTATG TCCCAAAGCCTGTGAGGGAA CAGGCTCTGGGAGCCGCTTC 1090       1100       1110       1120       1130       1140
CAGACTGTGGACTCGAGCAA CATTGATGGATTTGTGAACT GCACCAAGATCCTGGGCAAC 1150       1160       1170       1180       1190       1200
CTGGACTTTCTGATCACCGG CCTCAATGGAGACCCCTGGC ACAAGATCCCTGCCCTGGAC 1210       1220       1230       1240       1250       1260
CCAGAGAAGCTCAATGTCTT CCGGACAGTACGGGAGATCA CAGGTTACCTGAACATCCAG 1270       1280       1290       1300       1310       1320
TCCTGGCCGCCCCACATGCA CAACTTCAGTGTTTTTTCCA ATTTGACAACCATTGGAGGC 1330       1340       1350       1360       1370       1380
AGAAGCCTCTACAACCGGGG CTTCTCATTGTTGATCATGA AGAACTTGAATGTCACATCT 1390       1400       1410       1420       1430       1440
CTGGGCTTCCGATCCCTGAA GGAAATTAGTGCTGGGCGTA TCTATATAAGTGCCAATAGG 1450       1460       1470       1480       1490       1500
CAGCTCTGCTACCACCACTC TTTGAACTGGACCAAGGTGC TTCGGGGGCCTACGGAAGAG 1510       1520       1530       1540       1550       1560
CGACTAGACATCAAGCATAA TCGGCCGCGCAGAGACTGCG TGGCAGAGGGCAAAGTGTGT 1570       1580       1590       1600       1610       1620
GACCCACTGTGCTCCTCTGG GGGATGCTGGGGCCCAGGCC CTGGTCAGTGCTTGTCCTGT 1630       1640       1650       1660       1670       1680
CGAAATTATAGCCGAGGAGG TGTCTGTGTGACCCACTGCA ACTTTTTGAATGGGTACAGT 1690       1700       1710       1720       1730       1740
AAGGGGAGCCAGTCAAGGAT GGGTGGGGGTGGGGCCCTGC AATGGAACTGTTCAGGTGGC 1750       1760       1770       1780       1790       1800
ATACAATAAaagtctttaga caaaaaaaaaaaaaaaaaaa aaaaaaaaaaaaaaaaaaaa
```

FIG.1D (1) Information for SEQ ID NO:2:
    (i)      Sequence characteristics:
    (ii)     Length
    (iii)    Type
    (iv)     Molecule type
    (v)      Original source:
    (vi)     Organism: homo sapience p45-sErbB3 protein
AA 1-329: The N-terminal ErbB3 sequence
AA 1-19: signal peptide
AA 330-331: p45-sErbB3 unique sequence

```
              10                        20
MetArgAlaAsnAspAlaLeuGlnValLeu GlyLeuLeuPheSerLeuAlaArgGlySer>

30                        40
GluValGlyAsnSerGlnAlaValCysPro GlyThrLeuAsnGlyLeuSerValThrGly>

50                        60
AspAlaGluAsnGlnTyrGlnThrLeuTyr LysLeuTyrGluArgCysGluValValMet>

70                        80
GlyAsnLeuGluIleValLeuThrGlyHis AsnAlaAspLeuSerPheLeuGlnTrpIle>

90                       100
ArgGluValThrGlyTyrValLeuValAla MetAsnGluPheSerThrLeuProLeuPro>

110                       120
AsnLeuArgValValArgGlyThrGlnVal TyrAspGlyLysPheAlaIlePheValMet>

130                       140
LeuAsnTyrAsnThrAsnSerSerHisAla LeuArgGlnLeuArgLeuThrGlnLeuThr>

150                       160
GluIleLeuSerGlyGlyValTyrIleGlu LysAsnAspLysLeuCysHisMetAspThr>

170                       180
IleAspTrpArgAspIleValArgAspArg AspAlaGluIleValValLysAspAsnGly>

190                       200
ArgSerCysProProCysHisGluValCys LysGlyArgCysTrpGlyProGlySerGlu>

210                       220
AspCysGlnThrLeuThrLysThrIleCys AlaProGlnCysAsnGlyHisCysPheGly>

230                       240
ProAsnProAsnGlnCysCysHisAspGlu CysAlaGlyGlyCysSerGlyProGlnAsp>
```

FIG.1E

```
                             250                                    260
        ThrAspCysPheAlaCysArgHisPheAsn AspSerGlyAlaCysValProArgCysPro>

270                                    280
        GlnProLeuValTyrAsnLysLeuThrPhe GlnLeuGluProAsnProHisThrLysTyr>

290                                    300
        GlnTyrGlyGlyValCysValAlaSerCys ProHisAsnPheValValAspGlnThrSer>

310                                    320
        CysValArgAlaCysProProAspLysMet GluValAspLysAsnGlyLeuLysMetCys>

330
        GluProCysGlyGlyLeuCysProLysGly Gly
```

FIG.1F

P45-sErbB3 cDNA sequence (R2F)
nt 1-1048: The N-terminal ErbB3 sequence
nt 1049-1056: unique to p45-sErbB3
cgggcccccccctcgaggtcg ggccggacttggctgggctc ccttcaccctctgcggagtc

```
         70         80         90        100        110        120
ATGAGGGCGAACGACGCTCT GCAGGTGCTGGGCTTGCTTT TCAGCCTGGCCCGGGGCTCC 130        140        150        160        170        180
GAGGTGGGCAACTCTCAGGC AGTGTGTCCTGGGACTCTGA ATGGCCTGAGTGTGACCGGC 190        200        210        220        230        240
GATGCTGAGAACCAATACCA GACACTGTACAAGCTCTACG AGAGGTGTGAGGTGGTGATG 250        260        270        280        290        300
GGGAACCTTGAGATTGTGCT CACGGGACACAATGCCGACC TCTCCTTCCTGCAGTGGATT 310        320        330        340        350        360
CGAGAAGTGACAGGCTATGT CCTCGTGGCCATGAATGAAT TCTCTACTCTACCATTGCCC 370        380        390        400        410        420
AACCTCCGCGTGGTGCGAGG GACCCAGGTCTACGATGGGA AGTTTGCCATCTTCGTCATG 430        440        450        460        470        480
TTGAACTATAACACCAACTC CAGCCACGCTCTGCGCCAGC TCCGCTTGACTCAGCTCACC 490        500        510        520        530        540
GAGATTCTGTCAGGGGGTGT TTATATTGAGAAGAACGATA AGCTTTGTCACATGGACACA 550        560        570        580        590        600
ATTGACTGGAGGGACATCGT GAGGGACCGAGATGCTGAGA TAGTGGTGAAGGACAATGGC 610        620        630        640        650        660
AGAAGCTGTCCCCCCTGTCA TGAGGTTTGCAAGGGGCGAT GCTGGGGTCCTGGATCAGAA 670        680        690        700        710        720
GACTGCCAGACATTGACCAA GACCATCTGTGCTCCTCAGT GTAATGGTCACTGCTTTGGG 730        740        750        760        770        780
CCCAACCCCAACCAGTGCTG CCATGATGAGTGTGCCGGGG GCTGCTCAGGCCCTCAGGAC 790        800        810        820        830        840
ACAGACTGCTTTGCCTGCCG GCACTTCAATGACAGTGGAG CCTGTGTACCTCGCTGTCCA 850        860        870        880        890        900
CAGCCTCTTGTCTACAACAA GCTAACTTTCCAGCTGGAAC CCAATCCCCACACCAAGTAT 910        920        930        940        950        960
CAGTATGGAGGAGTTTGTGT AGCCAGCTGTCCCCATAACT TTGTGGTGGATCAAACATCC
```

FIG.1G

```
       970        980         990       1000        1010       1020
TGTGTCAGGGCCTGTCCTCC TGACAAGATGGAAGTAGATA AAAATGGGCTCAAGATGTGT 1030       1040        1050      1060        1070       1080
GAGCCTTGTGGGGGACTATG TCCCAAAGGTGGGTAGgaga tggtaagaagttgtaaagag 1090       1100        1110      1120        1130       1140
acagcctttcctctgagcct gcgcagaccaccccactga  acctctcttacatttgcagc 1150       1160        1170      1180        1190       1200
ctgtgagggaacaggctctg ggagccgcttccagactgtg gactcgagcaacattgatgg 1210       1220        1230      1240        1250       1260
atttgtgaactgcaccaaga tcctgggcaacctggacttt ctgatcaccggcctcaatgg 1270       1280        1290      1300        1310       1320
gttagagatcctgccttccc tccttagaccccagcccacg cacccctcacagttcatttc 1330       1340        1350      1360        1370       1380
attggccaaaactttcctat gtggagctgactaggaatca aagtcataaaattctagcct 1390       1400        1410      1420
gttacaaaggaaaaaaaaaa aaaaaaaaaaaaaaaaaaaa
```

FIG. 1H (2) Information for SEQ ID NO:3:
    (i)     Sequence characteristics:
    (ii)    Length
    (iii)   Type
    (iv)    Molecule type
    (v)     Original source:
    (vi)    Organism: homo sapience p75-sErbB3 protein (cDNA clone R35F)
AA 1-493: The N-terminal ErbB3 sequence
AA 1-19: signal peptide
AA 494-534: p75-sErbB3 unique sequence

```
                    10                              20
MetArgAlaAsnAspAlaLeuGlnValLeu GlyLeuLeuPheSerLeuAlaArgGlySer>

30                              40
GluValGlyAsnSerGlnAlaValCysPro GlyThrLeuAsnGlyLeuSerValThrGly>

50                              60
AspAlaGluAsnGlnTyrGlnThrLeuTyr LysLeuTyrGluArgCysGluValValMet>

70                              80
GlyAsnLeuGluIleValLeuThrGlyHis AsnAlaAspLeuSerPheLeuGlnTrpIle>

90                             100
ArgGluValThrGlyTyrValLeuValAla MetAsnGluPheSerThrLeuProLeuPro>

110                             120
AsnLeuArgValValArgGlyThrGlnVal TyrAspGlyLysPheAlaIlePheValMet>

130                             140
LeuAsnTyrAsnThrAsnSerSerHisAla LeuArgGlnLeuArgLeuThrGlnLeuThr>

150                             160
GluIleLeuSerGlyGlyValTyrIleGlu LysAsnAspLysLeuCysHisMetAspThr>

170                             180
IleAspTrpArgAspIleValArgAspArg AspAlaGluIleValValLysAspAsnGly>

190                             200
ArgSerCysProProCysHisGluValCys LysGlyArgCysTrpGlyProGlySerGlu>

210                             220
AspCysGlnThrLeuThrLysThrIleCys AlaProGlnCysAsnGlyHisCysPheGly>

230                             240
ProAsnProAsnGlnCysCysHisAspGlu CysAlaGlyGlyCysSerGlyProGlnAsp>
```

FIG.1I

```
                            250                                        260
ThrAspCysPheAlaCysArgHisPheAsn AspSerGlyAlaCysValProArgCysPro>
                            270                                        280
GlnProLeuValTyrAsnLysLeuThrPhe GlnLeuGluProAsnProHisThrLysTyr>
                            290                                        300
GlnTyrGlyGlyValCysValAlaSerCys ProHisAsnPheValValAspGlnThrSer>
                            310                                        320
CysValArgAlaCysProProAspLysMet GluValAspLysAsnGlyLeuLysMetCys>
                            330                                        340
GluProCysGlyGlyLeuCysProLysAla CysGluGlyThrGlySerGlySerArgPhe>
                            350                                        360
GlnThrValAspSerSerAsnIleAspGly PheValAsnCysThrLysIleLeuGlyAsn>
                            370                                        380
LeuAspPheLeuIleThrGlyLeuAsnGly AspProTrpHisLysIleProAlaLeuAsp>
                            390                                        400
ProGluLysLeuAsnValPheArgThrVal ArgGluIleThrGlyTyrLeuAsnIleGln>
                            410                                        420
SerTrpProProHisMetHisAsnPheSer ValPheSerAsnLeuThrThrIleGlyGly>
                            430                                        440
ArgSerLeuTyrAsnArgGlyPheSerLeu LeuIleMetLysAsnLeuAsnValThrSer>
                            450                                        460
LeuGlyPheArgSerLeuLysGluIleSer AlaGlyArgIleTyrIleSerAlaAsnArg>
                            470                                        480
GlnLeuCysTyrHisHisSerLeuAsnTrp ThrLysValLeuArgGlyProThrGluGlu>
                            490                                        500
ArgLeuAspIleLysHisAsnArgProArg ArgAspCysGlyGluGlyLysGlyLeuLeu>
                            510                                        520
GlyGlyGluAsnArgGluSerGlyArgArg GlyLeuLysGlyLeuPheCysProArgArg>
                            530       534
GlySerArgValGluGlyTrpAsnGlnGly GluGlyGlyCys
```

FIG. 1J

P75-sErbB3 cDNA sequence (clone R35F)
nt 1-1540: The N-terminal ErbB3 sequence
nt 1541-1665: unique to p75-sErbB3

```
         10         20         30         40         50         60
cggggccccccctcgaggtcg ggccggacttggctgggctc ccttcaccctctgcggagtc 70         80         90        100        110        120
ATGAGGGCGAACGACGCTCT GCAGGTGCTGGGCTTGCTTT TCAGCCTGGCCCGGGGCTCC 130        140        150        160        170        180
GAGGTGGGCAACTCTCAGGC AGTGTGTCCTGGGACTCTGA ATGGCCTGAGTGTGACCGGC 190        200        210        220        230        240
GATGCTGAGAACCAATACCA GACACTGTACAAGCTCTACG AGAGGTGTGAGGTGGTGATG 250        260        270        280        290        300
GGGAACCTTGAGATTGTGCT CACGGGACACAATGCCGACC TCTCCTTCCTGCAGTGGATT 310        320        330        340        350        360
CGAGAAGTGACAGGCTATGT CCTCGTGGCCATGAATGAAT TCTCTACTCTACCATTGCCC 370        380        390        400        410        420
AACCTCCGCGTGGTGCGAGG GACCCAGGTCTACGATGGGA AGTTTGCCATCTTCGTCATG 430        440        450        460        470        480
TTGAACTATAACACCAACTC CAGCCACGCTCTGCGCCAGC TCCGCTTGACTCAGCTCACC 490        500        510        520        530        540
GAGATTCTGTCAGGGGGTGT TTATATTGAGAAGAACGATA AGCTTTGTCACATGGACACA 550        560        570        580        590        600
ATTGACTGGAGGGACATCGT GAGGGACCGAGATGCTGAGA TAGTGGTGAAGGACAATGGC 610        620        630        640        650        660
AGAAGCTGTCCCCCCTGTCA TGAGGTTTGCAAGGGGCGAT GCTGGGGTCCTGGATCAGAA 670        680        690        700        710        720
GACTGCCAGACATTGACCAA GACCATCTGTGCTCCTCAGT GTAATGGTCACTGCTTTGGG 730        740        750        760        770        780
CCCAACCCCAACCAGTGCTG CCATGATGAGTGTGCCGGGG GCTGCTCAGGCCCTCAGGAC 790        800        810        820        830        840
ACAGACTGCTTTGCCTGCCG GCACTTCAATGACAGTGGAG CCTGTGTACCTCGCTGTCCA 850        860        870        880        890        900
CAGCCTCTTGTCTACAACAA GCTAACTTTCCAGCTGGAAC CCAATCCCCACACCAAGTAT
```

FIG.1K

```
       910         920         930         940         950         960
CAGTATGGAGGAGTTTGTGT AGCCAGCTGTCCCCATAACT TTGTGGTGGATCAAACATCC 970         980         990        1000        1010        1020
TGTGTCAGGGCCTGTCCTCC TGACAAGATGGAAGTAGATA AAAATGGGCTCAAGATGTGT 1030        1040        1050        1060        1070        1080
GAGCCTTGTGGGGGACTATG TCCCAAAGCCTGTGAGGGAA CAGGCTCTGGGAGCCGCTTC 1090        1100        1110        1120        1130        1140
CAGACTGTGGACTCGAGCAA CATTGATGGATTTGTGAACT GCACCAAGATCCTGGGCAAC 1150        1160        1170        1180        1190        1200
CTGGACTTTCTGATCACCGG CCTCAATGGAGACCCCTGGC ACAAGATCCCTGCCCTGGAC 1210        1220        1230        1240        1250        1260
CCAGAGAAGCTCAATGTCTT CCGGACAGTACGGGAGATCA CAGGTTACCTGAACATCCAG 1270        1280        1290        1300        1310        1320
TCCTGGCCGCCCCACATGCA CAACTTCAGTGTTTTTTCCA ATTTGACAACCATTGGAGGC 1330        1340        1350        1360        1370        1380
AGAAGCCTCTACAACCGGGG CTTCTCATTGTTGATCATGA AGAACTTGAATGTCACATCT 1390        1400        1410        1420        1430        1440
CTGGGCTTCCGATCCCTGAA GGAAATTAGTGCTGGGCGTA TCTATATAAGTGCCAATAGG 1450        1460        1470        1480        1490        1500
CAGCTCTGCTACCACCACTC TTTGAACTGGACCAAGGTGC TTCGGGGGCCTACGGAAGAG 1510        1520        1530        1540        1550        1560
CGACTAGACATCAAGCATAA TCGGCCGCGCAGAGACTGCG GTGAGGGAAAGGGTCTGCTA 1570        1580        1590        1600        1610        1620
GGTGGTGAGAATAGGGAGTC AGGGAGGAGAGGGCTGAAAG GACTATTCTGCCCTAGACGT 1630        1640        1650        1660        1670        1680
GGGAGTAGGGTTGAGGGATG GAACCAAGGAGAAGGGGGCT GTTAGgctggaagcagtaac 1690        1700        1710        1720        1730        1740
gaggaagaataatgaagaga gggcttgctgggagtcctca gactcctctcctaacccacc 1750        1760        1770        1780        1790        1800
ccttcctttccagtggcaga gggcaaagtgtgtgacccac tgtgctcctctgggggatgc 1810        1820        1830        1840        1850        1860
tggggcccaggccctggtca gtgcttgtcctgtcgaaatt atagccgaggaggtgtctgt
```

FIG.1L

```
          1870        1880        1890        1900        1910        1920
gtgacccactgcaactttct gaatgggtacagtaagggga gccagtcaaggatgggtggg 1930        1940        1950        1960        1970        1980
ggtggggccctgcaatggaa ctgttcaggtggcatacaat aaaagtctttagacagcaaa 1990        2000
aaaaaaaaaaaaaaaaaaaaaaaaa
```

FIG. 1M (3) Information for SEQ ID NO:4:
    (i)     Sequence characteristics:
    (ii)    Length
    (iii)   Type
    (iv)    Molecule type
    (v)     Original source:
    (vi)    Organism: homo sapience p50-sErbB3 protein (cDNA clone R1F)
AA 1-370: The N-terminal ErbB3 sequence
AA 1-19: signal peptide
AA 371-390: p50-sErbB3 unique sequence

```
                     10                                    20
MetArgAlaAsnAspAlaLeuGlnValLeu  GlyLeuLeuPheSerLeuAlaArgGlySer>

30                                    40
GluValGlyAsnSerGlnAlaValCysPro  GlyThrLeuAsnGlyLeuSerValThrGly>

50                                    60
AspAlaGluAsnGlnTyrGlnThrLeuTyr  LysLeuTyrGluArgCysGluValValMet>

70                                    80
GlyAsnLeuGluIleValLeuThrGlyHis  AsnAlaAspLeuSerPheLeuGlnTrpIle>

90                                   100
ArgGluValThrGlyTyrValLeuValAla  MetAsnGluPheSerThrLeuProLeuPro>

110                                   120
AsnLeuArgValValArgGlyThrGlnVal  TyrAspGlyLysPheAlaIlePheValMet>

130                                   140
LeuAsnTyrAsnThrAsnSerSerHisAla  LeuArgGlnLeuArgLeuThrGlnLeuThr>

150                                   160
GluIleLeuSerGlyGlyValTyrIleGlu  LysAsnAspLysLeuCysHisMetAspThr>

170                                   180
IleAspTrpArgAspIleValArgAspArg  AspAlaGluIleValValLysAspAsnGly>

190                                   200
ArgSerCysProProCysHisGluValCys  LysGlyArgCysTrpGlyProGlySerGlu>

210                                   220
AspCysGlnThrLeuThrLysThrIleCys  AlaProGlnCysAsnGlyHisCysPheGly>

230                                   240
ProAsnProAsnGlnCysCysHisAspGlu  CysAlaGlyGlyCysSerGlyProGlnAsp>
```

FIG.1N

```
                                      250                                    260
        ThrAspCysPheAlaCysArgHisPheAsn AspSerGlyAlaCysValProArgCysPro>

270                                    280
        GlnProLeuValTyrAsnLysLeuThrPhe GlnLeuGluProAsnProHisThrLysTyr>

290                                    300
        GlnTyrGlyGlyValCysValAlaSerCys ProHisAsnPheValValAspGlnThrSer>

310                                    320
        CysValArgAlaCysProProAspLysMet GluValAspLysAsnGlyLeuLysMetCys>

330                                    340
        GluProCysGlyGlyLeuCysProLysAla CysGluGlyThrGlySerGlySerArgPhe>

350                                    360
        GlnThrValAspSerSerAsnIleAspGly PheValAsnCysThrLysIleLeuGlyAsn>

370                                    380
        LeuAspPheLeuIleThrGlyLeuAsnGly LeuGluIleLeuProSerLeuLeuArgPro>

380                                    390
        GlnProThrHisProSerGlnPheIleSer LeuAlaLysThrPheLeuCysGlyAlaAsp
```

FIG.10 p50-sErbB3 cDNA sequence (R1F)
nt 1-1169: The N-terminal ErbB3 sequence
nt 1170-1263: unique to p50-sErbB3

```
         10            20            30            40            50            60
cgggccccccctcgaggtcg  ggccggacttggctgggctc  ccttcaccctctgcggagtc 70            80            90           100           110           120
ATGAGGGCGAACGACGCTCT  GCAGGTGCTGGGCTTGCTTT  TCAGCCTGGCCCGGGGCTCC 130           140           150           160           170           180
GAGGTGGGCAACTCTCAGGC  AGTGTGTCCTGGGACTCTGA  ATGGCCTGAGTGTGACCGGC 190           200           210           220           230           240
GATGCTGAGAACCAATACCA  GACACTGTACAAGCTCTACG  AGAGGTGTGAGGTGGTGATG 250           260           270           280           290           300
GGGAACCTTGAGATTGTGCT  CACGGGACACAATGCCGACC  TCTCCTTCCTGCAGTGGATT 310           320           330           340           350           360
CGAGAAGTGACAGGCTATGT  CCTCGTGGCCATGAATGAAT  TCTCTACTCTACCATTGCCC 370           380           390           400           410           420
AACCTCCGCGTGGTGCGAGG  GACCCAGGTCTACGATGGGA  AGTTTGCCATCTTCGTCATG 430           440           450           460           470           480
TTGAACTATAACACCAACTC  CAGCCACGCTCTGCGCCAGC  TCCGCTTGACTCAGCTCACC 490           500           510           520           530           540
GAGATTCTGTCAGGGGGTGT  TTATATTGAGAAGAACGATA  AGCTTTGTCACATGGACACA 550           560           570           580           590           600
ATTGACTGGAGGGACATCGT  GAGGGACCGAGATGCTGAGA  TAGTGGTGAAGGACAATGGC 610           620           630           640           650           660
AGAAGCTGTCCCCCCTGTCA  TGAGGTTTGCAAGGGGCGAT  GCTGGGGTCCTGGATCAGAA 670           680           690           700           710           720
GACTGCCAGACATTGACCAA  GACCATCTGTGCTCCTCAGT  GTAATGGTCACTGCTTTGGG 730           740           750           760           770           780
CCCAACCCCAACCAGTGCTG  CCATGATGAGTGTGCCGGGG  CTGCTCAGGCCCTCAGGAC 790           800           810           820           830           840
ACAGACTGCTTTGCCTGCCG  GCACTTCAATGACAGTGGAG  CCTGTGTACCTCGCTGTCCA 850           860           870           880           890           900
CAGCCTCTTGTCTACAACAA  GCTAACTTTCCAGCTGGAAC  CCAATCCCCACACCAAGTAT
```

FIG.1P

```
       910        920        930        940        950        960
CAGTATGGAGGAGTTTGTGT AGCCAGCTGTCCCCATAACT TTGTGGTGGATCAAACATCC 970        980        990       1000       1010       1020
TGTGTCAGGGCCTGTCCTCC TGACAAGATGGAAGTAGATA AAAATGGGCTCAAGATGTGT 1030       1040       1050       1060       1070       1080
GAGCCTTGTGGGGGACTATG TCCCAAAGCCTGTGAGGGAA CAGGCTCTGGGAGCCGCTTC 1090       1100       1110       1120       1130       1140
CAGACTGTGGACTCGAGCAA CATTGATGGATTTGTGAACT GCACCAAGATCCTGGGCAAC 1150       1160       1170       1180       1190       1200
CTGGACTTTCTGATCACCGG CCTCAATGGGTTAGAGATCC TGCCTTCCCTCCTTAGACCC 1210       1220       1230       1240       1250       1260
CAGCCCACGCACCCCTCACA GTTCATTTCATTGGCCAAAA CTTTCCTATGTGGAGCTGAC 1270       1280       1290       1300       1310       1320
TAGgaatcaaagtcataaaa ttctagcctgttaaaaaaaa aaaaaaaaaaaaaaaaaaaa
```

FIG. 1Q

SOLUBLE ERBB3 RECEPTOR ISOFORMS

This application claims priority from U.S. application Ser. No. 60/294,824 filed May 31, 2001 entitled, "Use of Secreted Human ErbB3 Receptor Isoform to Inhibit Heregulin Simulated Activation of ErbB2, ErbB3 and ErbB4", which is included herein by reference.

The disclosed invention was made with the support of a grant from the National Cancer Institute (CA85133). The United States Government has certain rights in the invention.

FIELD OF INVENTION

The present invention is directed to a system and method that uses soluble ErbB3 (sErbB3) proteins, including p85-sErbB3, p45-sErbB3 and other isoforms of sErbB3, wherein said sErbB3 protein binds to heregulins and antagonizes heregulin-stimulated activation of the ErbB receptors and blocks the cell proliferative activity thereof. The present invention is also directed to expression vectors encoding a sErbB3 protein, including p85-sErbB3, p45-sErbB3 and other isoforms of sErbB3, host cells harboring such expression vectors, methods of preparing such proteins, and methods and systems utilizing such proteins for the treatment of conditions associated with undesired heregulin stimulation.

BACKGROUND OF THE INVENTION

The heregulins (also called neuregulins, neu differentiation factor (NDF), acetylcholin receptor inducing activity (ARIA), glial growth factors (GGFs)) are a family of epidermal growth factor-like growth factors that activate members of the ErbB/EGF receptor family (Holmes, Sliwkowski et al. 1992; Peles, Bacus et al. 1992; Wen, Peles et al. 1992; Falls, Rosen et al. 1993; Marchionni, Goodearl et al. 1993). Isoforms of heregulins, all of which arise from splice variants of a single gene, NRG-1 (neuregulin-1), have been cloned and classified into the α and β subgroups based on structural differences in their EGF binding domains (Holmes, Sliwkowski et al. 1992).

ErbB3-mediated signal transduction exerted by heregulins has been implicated in the regulation of diverse biological events including Schwann cell differentiation, neural regulation of skeletal muscle differentiation, heart development, and proliferation and differentiation of normal and malignant breast epithelial cells (Alroy and Yarden 1997; Sundaresan, Penuel et al. 1999). Research has shown that breast carcinoma cells respond to heregulin through proliferation, differentiation, as well as morphogenesis. Carcinoma cells expressing heregulin are hormone-independent and correlated to the ability for metastasis in experimental studies.

ErbB3 is a transmembrane glycoprotein encoded by the c-erbB3 gene (Kraus, Issing et al. 1989; Plowman, Whitney et al. 1990). The ErbB3 receptor belongs to the ErbB family which is composed of four growth factor receptor tyrosine kinases, known as ErbB1/EGFR, ErbB2/Neu, ErbB4, as well as ErbB3. ErbB3 and ErbB4 are receptors for heregulins and ErbB2 is a coreceptor (Carraway and Burden 1995). These receptors are structurally related and include three functional domains: an extracellular ligand-binding domain, a transmembrane domain, and a cytoplasmic tyrosine kinase domain (Plowman, Culouscou et al. 1993). The extracellular domain can be further divided into four subdomains (I-IV), including two cysteine-rich regions (II and IV) and two flanking regions (I and III). The ErbB3 is unusual among receptor tyrosine kinases in that its catalytic domain is defective. Despite its lack of intrinsic catalytic activity, ErbB3 is an important mediator of heregulin responsiveness. Heregulin binding induces ErbB3 to associate with other members of the ErbB family to form heterodimeric receptor complexes. ErbB3 then transactivates the kinase of its partner receptor which initiates a variety of cytoplasmic signaling cascades.

The ErbB3 receptor, together with ErbB2, is an important receptor involved in cellular growth and differentiation. Particular attention has focused on the role of ErbB3 as a coreceptor of ErbB2 in the area of cancer research. Transgenic mice that have been engineered to overexpress heregulin in mammary glands have been reported to exhibit persistent terminal end buds and, over time, to develop mammary adenocarcinomas (Krane and Leder 1996). ErbB3 expression studies on tumor tissues and on cell lines show frequent co-expression of ErbB2 and ErbB3 receptors (Alimandi, Heidaran et al. 1995; Meyer and Birchmeier 1995; Robinson, He et al. 1996; Siegel, Ryan et al. 1999). In addition, both ErbB2 and ErbB3 are activated in mammary tumors formed in transgenic mice harboring only the activated form of ErbB2 (Siegel, Ryan et al. 1999). A lot of cell lines used for experimental tumor formation studies are either estrogen-dependent (MCF-7 and T47D, the low ErbB2 expressers) or estrogen-independent (SKBR3, high ErbB2 expressers). However, these cell lines do not exhibit metastatic phenotypes. When MCF-7 cells are transfected to overexpress ErbB2, MCF-7 cells gain estrogen-independent phenotype, however, they never metastasize. On the other hand, the MCF-7 cells overexpressing heregulin gains metastatic phenotype, suggesting heregulin's active role in metastasis (Hijazi, Thompson et al. 2000; Tsai, Hornby et al. 2000).

Five alternate ErbB3 transcripts arise from read-through of an intron and the use of alternative polyadenylation signals (Lee and Maihle 1998; Katoh, Yazaki et al. 1993). Using 3'-RACE the inventors have isolated four novel c-erbB3 cDNA clones of 1.6, 1.7, 2.1, and 2.3 kb from a human ovarian carcinoma-derived cell line (Lee and Maihle 1998). p85-sErbB3 of 543 aa, encoded by a 2.1 kb alternate c-erbB3 transcript (cDNA clone R31F), is composed of subdomains I through III and the first third of subdomain IV, and has a unique 24 amino acid carboxy-terminal sequence. p45-sErbB3 of 312 aa, encoded by a 1.7 kb alternate c-erbB3 transcript (cDNA clone R2F) contains subdomains I, II, and a portion of subdomain III of the extracellular domain of ErbB-3 followed by two unique glycine residues. p50-sErbB3 of 381 aa, encoded by a 1.6 kb alternate c-erbB3 transcript (cDNA clone R1F) contains subdomains I, II, and a portion of subdomain III of the extracellular domain of ErbB-3 followed by 30 unique amino acids. p75-sErbB3 of 515 aa, encoded by a 2.3 kb alternate c-erbB3 transcript (cDNA clone R35F), is composed of subdomains I through III, and has a unique 41 amino acid carboxy-terminal sequence (FIG. 1) (Lee and Maihle 1998).

Using various recombinant soluble forms of EGFR, it has been shown that efficient inhibition of full-length EGFR activation by dominant-negative heterodimerization occurs only when these deletion mutants retain the transmembrane domain in addition to the extracellular domain (Redemann, Holzmann et al. 1992). Similarly, a recombinant dominant-negative ErbB3 mutant with a deleted cytoplasmic domain but which retains its transmembrane domain can inhibit full-length ErbB2 and ErbB3 activation (Ram, Schelling et al. 2000). In contrast, in avian tissues, expression of a naturally occurring sEGFR/ErbB1 inhibits TGFα dependent transformation (Flickinger, Maihie et al. 1992). Soluble EGFR secreted by the A431 human carcinoma cell line also has been reported to inhibit the kinase activity of purified full-length EGFR in a ligand-independent manner (Basu, Raghunath et al. 1989). In no case do these soluble EGF/ErbB1 receptors function as antagonists through high affinity ligand-binding. Similarly, herstatin, a naturally occurring soluble ErbB2 protein which inhibits ErbB2 activation appears to function by blocking ErbB2 dimerization (Doherty, Bond et al. 1999).

The ErbB3 protein, specifically the p85-sErbB3 and p45 sErbB3 isoforms, is unique among other naturally occurring or recombinant soluble ErbB receptors in that it binds specifically to heregulin with high affinity and inhibits its binding to cell surface receptors and consequently inhibit heregulin-induced activation of the receptors and their downstream effectors. Thus sErbB3, specifically p85-sErbB3 and p45-sErbB3, can be used as a therapeutic reagent for heregulin-induced malignancy such as mammary and prostate tumors.

Heretofore, production and purification methods for, therapeutic uses of, and useful compositions containing, this protein, referred to herein as p85-sErbB3 have not been available.

SUMMARY OF THE INVENTION

The present invention provides several novel isolated and purified nucleic acids which encode soluble isoforms of ErbB3. Preferred embodiments of this aspect of the invention are nucleic acid sequences which specifically encode a soluble form of ErbB3 whose amino acid sequence comprises the sequence of SEQ ID NO: 2. The nucleic acid embodiments include DNA SEQ ID NO: 1. comprises the sequence of SEQ ID NO: 1. The nucleic acid embodiments include DNA SEQ ID NO:2

The present invention discloses a system and process that uses isoforms of sErbB3 to bind to HRG with high affinity and effectively block HRG binding to cell surface receptors. More specifically, the present invention discloses a system and process that uses p85-sErbB3 to bind to HRG with high affinity and substantially block HRG binding to cell surface receptors. The present invention also discloses the diagnosis and treatment of carcinoma cells with p85-sErbB3 and other ErbB3 isoforms.

A preferred embodiment of the present invention uses an expression vector, such as a plasmid or virus, containing the isolated cDNA encoding p85-sErbB3 and other ErbB3 isoforms, as well as a cell, either eukaryotic or prokaryotic, containing the expression vector.

The present invention also discloses a process for producing the p85-sErbB3 molecule and other ErbB3 isoforms, which includes the steps of ligating the isolated DNA into an expression vector capable of expressing the isolated DNA in a suitable host; transforming the host with the expression vector; culturing the host under conditions suitable for expression of the isolated DNA and production of the p85-sErbB3 protein and other ErbB3 isoforms, and isolating the protein from the host. The host cell may be a prokaryote, or a eukaryote.

The invention further discloses a method and system for the production of polyclonal or monoclonal antibodies directed against unique p85-sErbB3 and other ErbB isoform epitopes. The inventors have generated polyclonal antibodies specific to p85-sErbB3 using a C-terminal unique sequence of the p85-sErbB3 as an antigen. The affinity-purified antibody can be used to detect p85-sErbB3 using immunoblot analysis and other detection methods.

Another embodiment of the invention discloses a system and method of detecting p85-sErbB3 and other ErbB3 isoforms in a mammalian biological specimen which is selected from the group consisting of fluids (including blood, serum, plasma, urine and ascites), tissues, and their derivatives. Further the inventors disclose an immunoprecipitation followed by immunoblot analysis to detect p85-sErbB3 using anti-ErbB3 antibodies.

Yet another embodiment of this invention provides a vector for gene therapy, comprising a nucleic acid molecule having i) a transcription regulatory segment; and ii) a second segment coding for p85-sErbB3 or other ErbB3 isoforms under transcriptional control of the transcription regulatory sequence; and a delivery vehicle for delivering the nucleic acid molecule.

Other aspects, embodiments, features and advantages of the present invention will be apparent from a reading of the description of the following preferred embodiments.

BRIEF DESCRIPTION OF THE FIGURES AND DEFINITIONS

FIG. 1. Diagram of soluble ErbB3 (sErbB3) proteins. ErbB3 is composed of a 19 aa signal peptide sequence that is cleaved (gray box), an extracellular ligand-binding domain (aa 1-620), a transmembrane domain (aa 621-646; indicated as TM), and an intracellular domain (aa 647-1323). The extracellular domain of the receptor can be further divided into four subdomains (I-IV), as noted in the text. The alternate c-erbB3 transcripts arise from read-through of an intron and the use of alternative polyadenylation signals. p45-sErbB3 contains the amino-terminal 310 amino acids of ErbB3 and two unique carboxy-terminal amino acid residues. p50-sErbB3 contains the amino-terminal 351 amino acids of ErbB3 and 30 unique carboxy-terminal amino acid residues. p75-sErbB3 contains the amino-terminal 474 amino acids of ErbB3 and 41 unique carboxy-terminal amino acid residues. p85-sErbB3 contains the amino-terminal 519 amino acids of ErbB3 and 24 unique carboxy-terminal amino acid residues. The carboxy-terminal unique sequences are denoted as black boxes.

Figure 2:
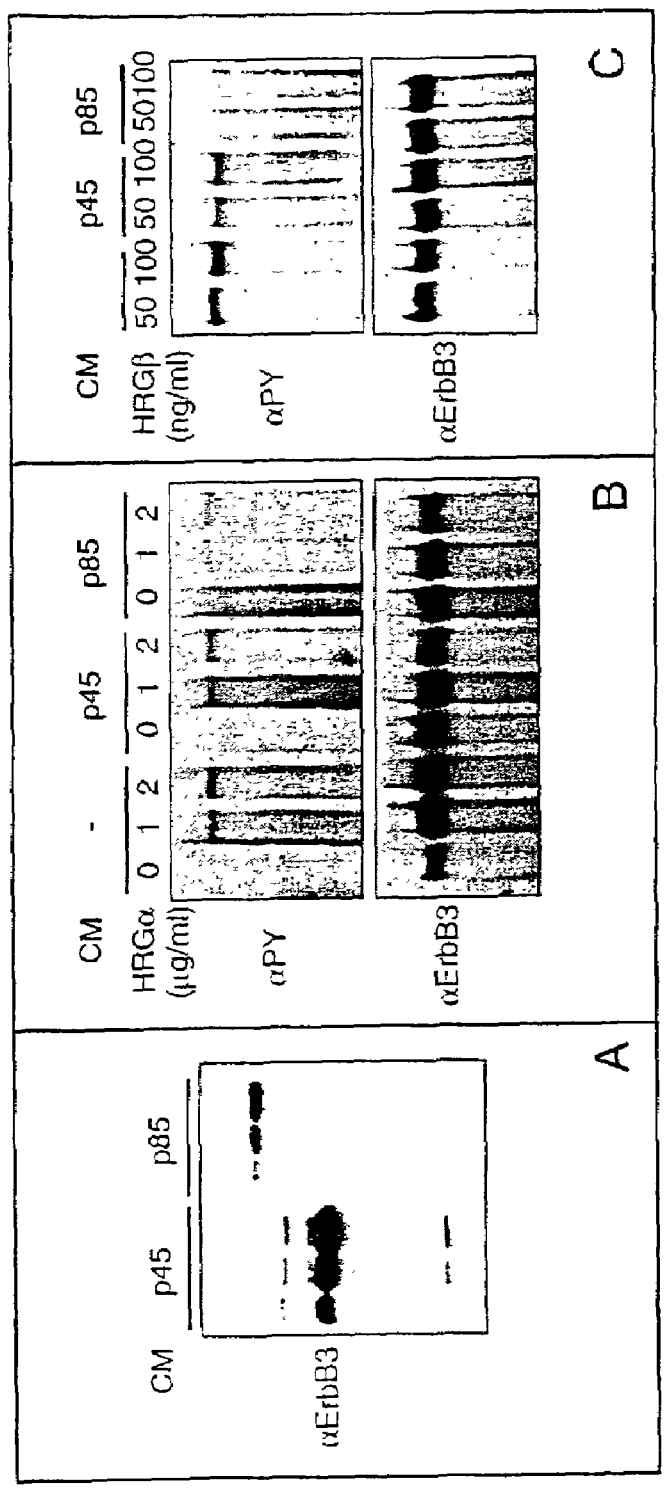

FIG. 2. p45-sErbB3 and p85-sErbB3 in conditioned media can block HRG-induced activation of ErbB3. (A) p45-sErbB3 and p85-sErbB3 in the concentrated conditioned media were detected by Western blotting using an anti-ErbB3 antibody recognizing the extracellular region of ErbB3. Increasing volumes (5, 10, 20 µl; left to right) of the concentrated conditioned media (×15) were loaded on an SDS-PAGE gel. (B) and (C) The Ba/F3 (ErbB2+ErbB3) cells were stimulated with HRGα (panel B) and HRGβ (panel C) with or without the concentrated conditioned media for 10 min at room temperature prior to lysis. ErbB3 was immunoprecipitated with an anti-ErbB3 antibody from equal amounts of total protein, subjected to SDS-PAGE, and analyzed by Western blotting using an anti-phosphotyrosine antibody (αPY). Filters were stripped and reprobed with anti-ErbB3 antibody recognizing the intracellular region of ErbB3.

Figure 3:
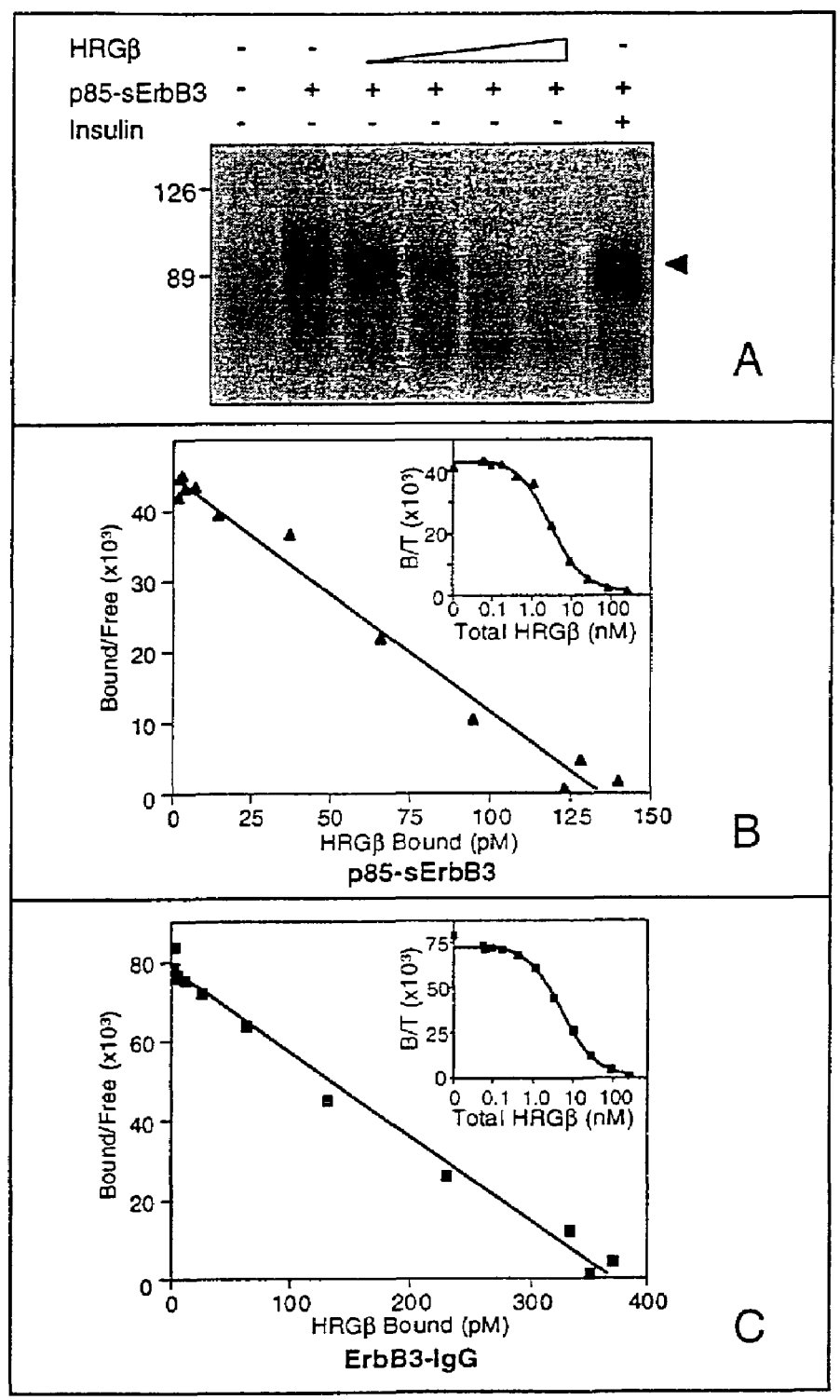

FIG. 3. p85-sErbB3 binds to HRG. (A) HRGβ was crosslinked to p85-sErbB3 (25 nM) with $BS^3$ after incubating in the presence of 50 nM $^{125}$I-HRGβ without or with increasing concentrations (0.16, 0.32, 0.64, 1.25 µM) of unlabeled HRGβ. Insulin (1.25 µM) was used as a negative control. The arrowhead indicates a 90 kDa complex of $^{125}$I-HRGβ and p85-sErbB3. (B) and (C) Binding analysis of $^{125}$1-HRG to p85-sErbB3 and ErbB3-IgG fusion protein. Binding assays were performed in a 96-well plate format as described in Materials and Methods. Binding results were analyzed by using Scatchard method and by plotting the displacement of $^{125}$I-HRGβ$_{177-244}$ binding by unlabeled HRGβ$_{177-244}$ (Inset).

Figure 4:
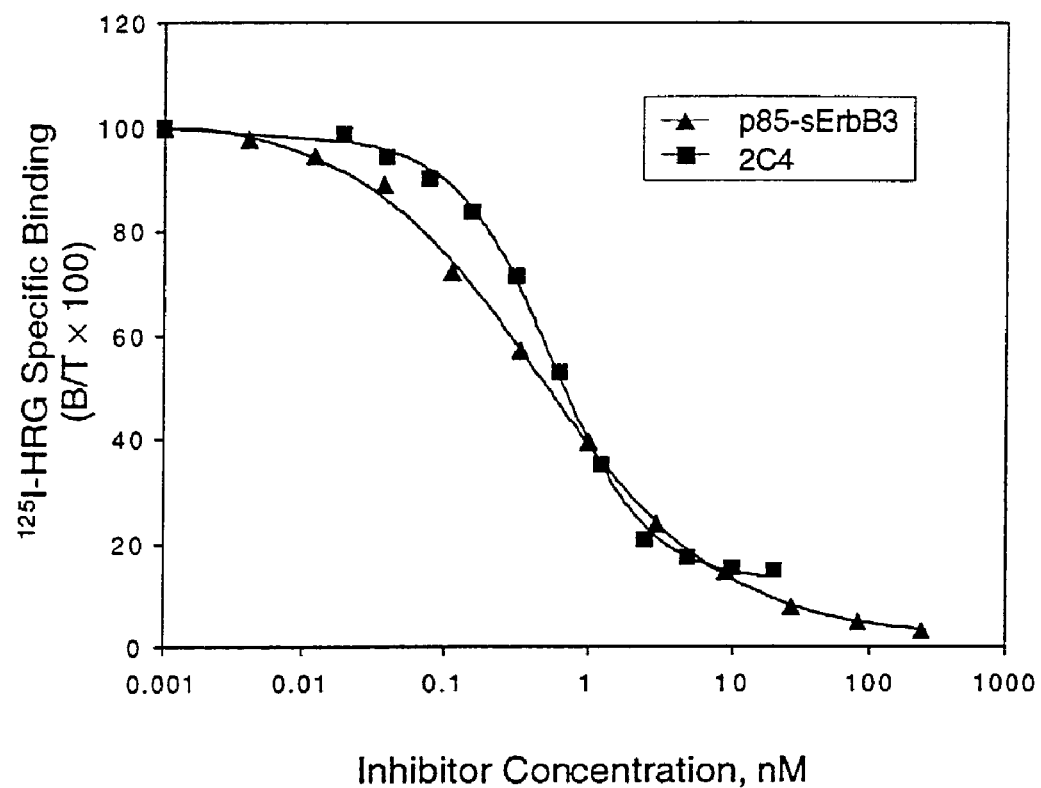

FIG. 4. Inhibition of HRGβ binding by p85-sErbB3 and by 2C4, a monoclonal antibody specific for ErbB2. T47D cells were incubated with the indicated concentrations of p85- sErbB3 and 2C4 at room temperature for 30 min. $^{125}$I-HRGβ$_{177-244}$ (0.1 nM) was then added and binding reactions were performed as described in Materials and Methods. $^{125}$I-HRGβ$_{177-244}$ bound to the cell surface was measured using a gamma counter.

Figure 5:
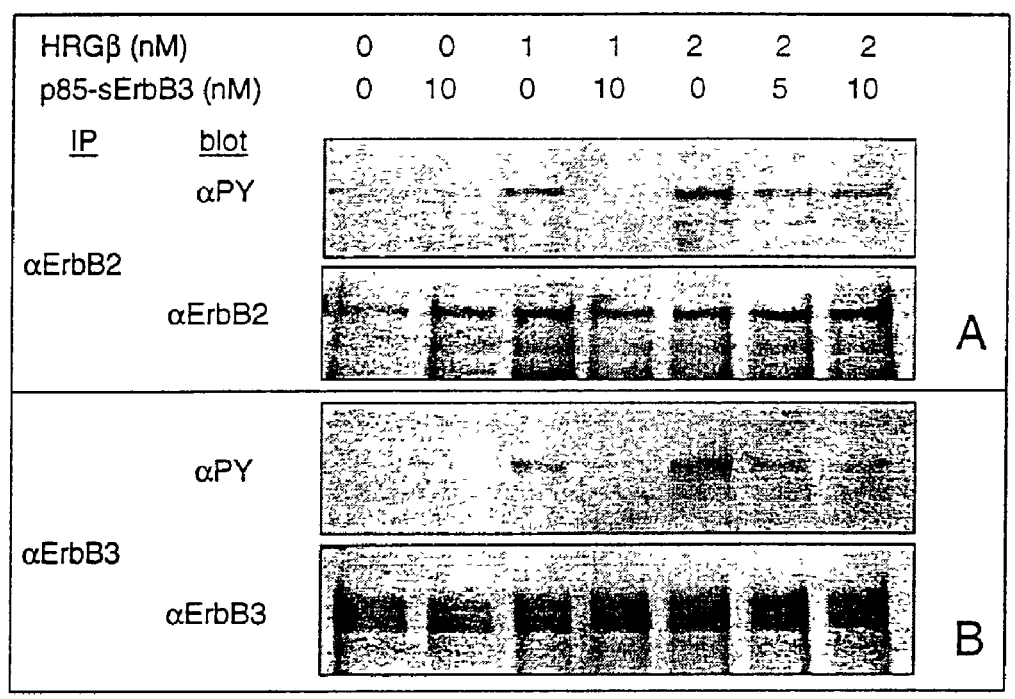

FIG. 5. p85-sErbB3 blocks HRG-induced activation of ErbB2 and ErbB3 in the Ba/F3 (ErbB2+ErbB3) cells. Cells were untreated or stimulated with HRGβ$_{1-241}$ alone or HRGβ$_{1-241}$ plus purified p85-sErbB3 for 10 min at room temperature. Receptor phosphorylation levels and ErbB2 and ErbB3 receptor levels were determined by anti-ErbB2 (A) and anti-ErbB3 (B) immunoprecipitation followed by Western blotting as described in FIG. 2.

Figure 6:
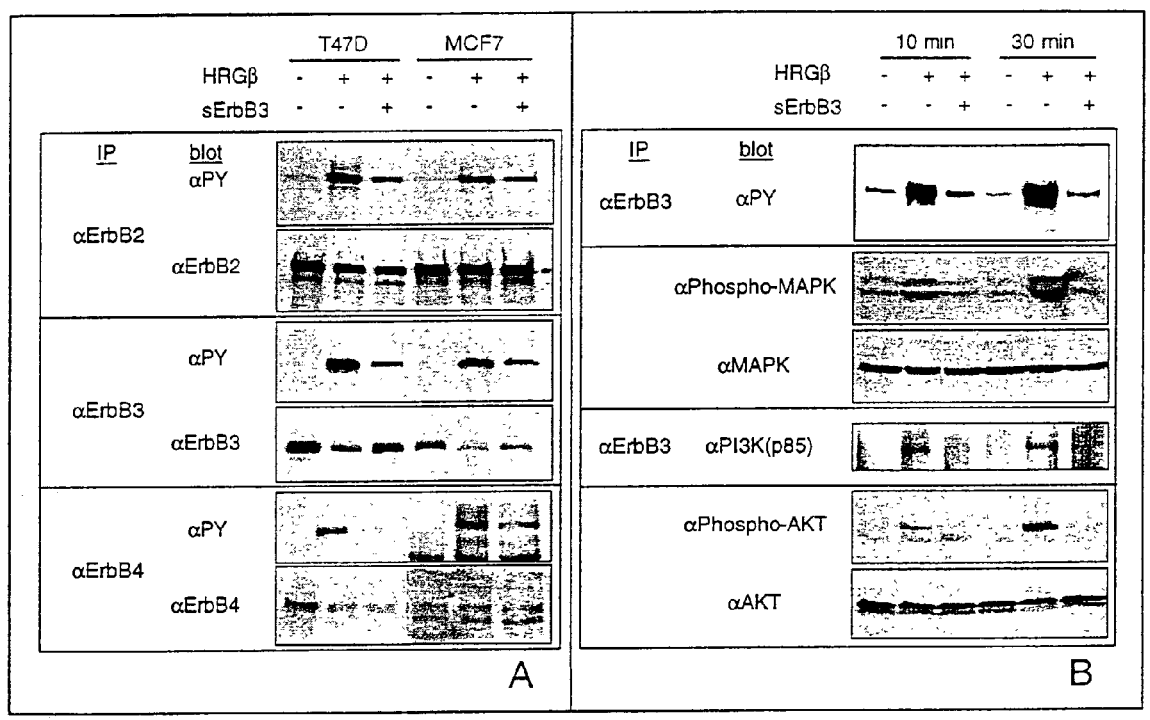

FIG. 6. p85-sErbB3 blocks HRG-induced activation of ErbB proteins and their downstream activators MAPK, PI3K (p85), and Akt. (A) p85-sErbB3 blocks HRG-induced activation of ErbB2, ErbB3, and ErbB4 in T47D and MCF7 breast carcinoma cells. Serum-starved cells were stimulated with no HRGβ, HRGβ alone, or 6 nM HRGβ plus 36 nM p85-sErbB3 for 10 min at room temperature. Receptor phosphorylation levels and ErbB2, ErbB3, and ErbB4 receptor levels were determined by immunoprecipitation followed by Western blotting. (B) p85-sErbB3 inhibits HRG-induced association of PI3K (p85) with ErbB3 and activation of MAPK and Akt in T47D cells. Cells were treated with 1 nM HRGβ and 10 nM p85-sErbB3 for 10 min or 30 min and analyzed for activation of ErbB3. Association of PI3K (p85) with ErbB3 was analyzed by immunoprecipitation of cell lysates using an anti-ErbB3 antibody followed by Western blotting of anti-PI3K (p85) antibody. Activation of MAPK and Akt was examined by Western blotting of cell lysates using antibodies specific to phospho-MAPK and phospho-Akt.

Figure 7:
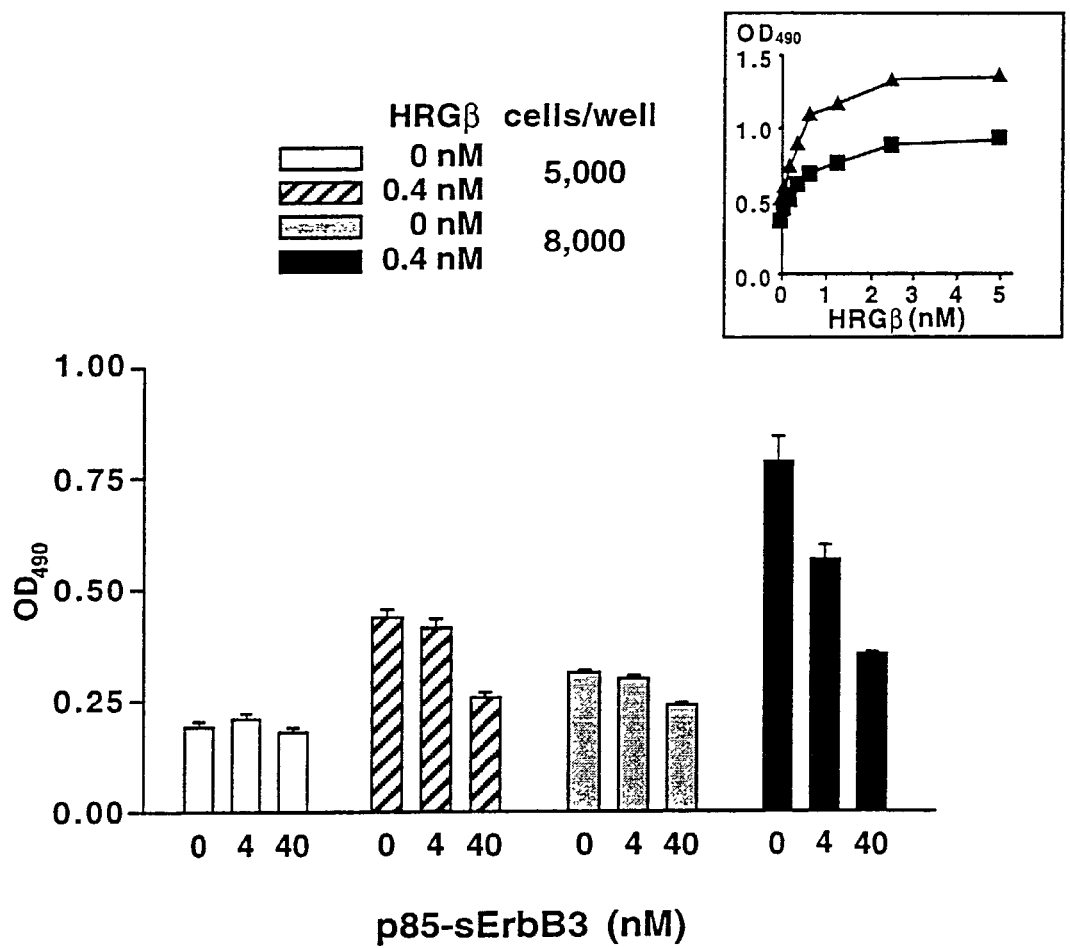

FIG. 7. p85-sErbB3 inhibits cell growth stimulation by HRG. MCF7 cells were trypsinized, washed, and plated at a density of 5,000 (squares) or 8,000 cells/well (triangles) in 96-well plates with increasing concentrations of HRGβ in serum-free medium and growth was measured after 3 days (inset). MCF7 cells were trypsinized, washed, incubated with p85-sErbB3 for 30 min, and plated with or without 0.4 nM HRGβ in serum-free medium. At 40 nM (a 100-fold molar excess to HRGβ) in the presence of HRGβ, p85-sErbB3 inhibited cell growth by 75% and 90%, at densities of 5,000 and 8,000 cells/well, respectively, whereas the same concentration of p85-sErbB3 did not affect cell growth in the absence of HRGβ. The data presented are the mean±standard deviation of six replicates. This experiment was repeated three times and the results shown represent all three trials.

DEFINITIONS

As used herein, the term "soluble" ErbB3 (sErbB3) means that the ErbB3 polypeptide is found in a form that is not anchored to the membrane of a cell, i.e., a portion of the sErbB3 is not found physically embedded in the lipid bilayer which comprises the cell membrane in the organism of its origin. As used herein, the term "biological activity" of a peptide of the invention is defined to mean a polypeptide comprising a subunit of a peptide having SEQ ID NO: 2, or a variant thereof, which has at least about 10%, preferably at least about 50%, and more preferably at least about 90%, of the activity of a peptide having SEQ ID NO: 2. The activity of a peptide of the invention can be measured by methods well known in the art including, but not limited to, the ability to bind heregulins, or the ability of the peptide to elicit a sequence-specific immune response when the peptide is administered to an organism, e.g., goat, sheep or mice.

The terms "recombinant nucleic acid" or "preselected nucleic acid," e.g., "recombinant DNA sequence or segment" or "preselected DNA sequence or segment" refer to a nucleic acid that has been derived or isolated from any appropriate tissue source and that may be subsequently chemically altered, typically in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

"Regulatory sequences" is defined to mean RNA or DNA sequences necessary for the expression, post-transcriptional modification, translation, and post-translational modification of an operably linked coding sequence in a particular host organism. The control sequences that are suitable for prokaryotic cells, for example, include a promoter, and optionally an operator sequence, and a ribosome binding site. Eukaryotic cells are known to utilize promoters, stop sequences, enhancers, splicing, and polyadenylation signal sequences, as well as glycosylation and secretory signal sequences.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including avian, plant, insect, yeast, fungal or bacterial sources. Generally, the preselected DNA sequence is related to a DNA sequence that is resident in the genome of the host cell but is not expressed, or not highly expressed, or, alternatively, over-expressed.

The terms "transfected" or "transformed" are used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered DNA," "non-native DNA," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding an sErbB3 isoform, which host cell may or may not express significant levels of autologous or "native" ErbB3 isoforms.

DESCRIPTION OF THE INVENTION

Using various recombinant soluble forms of EGFR, it has been shown that efficient inhibition of full-length EGFR activation by dominant-negative heterodimerization occurs only when these deletion mutants retain the transmembrane domain and the extracellular domain. Similarly, a recombinant dominant-negative ErbB3 mutant with a deleted cytoplasmic domain but which retains its transmembrane domain can inhibit full-length ErbB2 and ErbB3 activation. In contrast, in avian tissues, expression of a naturally occurring sEGFR/ErbB 1 inhibits TGFα dependent transformation. Soluble EGFR secreted by the A43 1 human carcinoma cell line also has been reported to inhibit the kinase activity of purified full-length EGFR in a ligand-independent manner. These soluble EGF/ErbB 1 receptors do not function as antagonists through high affinity ligand-binding. Similarly, herstatin, a naturally occurring soluble ErbB2 protein which inhibits ErbB2 activation appears to function by blocking ErbB2 dimerization; this The physiological role of p85-sErbB3 in normal tissues also has not been understood. The present invention indicates that although a much higher concentration (100-fold) was required to inhibit cell growth, a 10-fold molar excess of p85-sErbB3 was sufficient for inhibition of phosphorylation of ErbB receptors. At this ratio, a small fraction of receptors are still activated and are enough for growth stimulation. It is known that the 2.1 kb transcript encoding p85-sErbB3 is expressed at low levels compared to the full-length c-erbB3 transcript in all cell lines and tissues examined to date, however, local expression of this transcript has not been studied in detail. It is, therefore, plausible that p85-sErbB3 acts as an HRG antagonist locally in a tissue-specific and/or stage-specific manner, and related studies to examine the distribution of p85-sErbB3 in selected tissues are currently underway. Evidence suggests that local concentrations of autocrine growth factors such as EGF are exquisitely regulated and do not travel far from the cell surface from which they are released. In this context, tightly regulated levels of local p85-sErbB3 expression have important consequences for HRG-mediated cell growth. These consequences are even more dramatic in cancer cells where cell polarity is typically lost, resulting in deregulation of normal spatial and temporal control of growth factor:receptor interactions.

The present invention provides several novel isolated and purified nucleic acids which encode isoforms of ErbB3 and nucleic acids encoding engineered variants of these proteins. Preferred embodiments are nucleic acids which specifically encode isoforms of ErbB3 whose amino acid sequence comprises the sequence of SEQ ID NO: 4 and SEQ ID NO: 2. The present invention also defines the biochemical and biological characteristics of a novel sErbB3 isoform designated p85-sErbB3. The present invention discloses the use of p85-sErbB3 as a unique HRG inhibitor because it can block HRG binding to cell surface receptors via binding to HRG with high affinity, thereby, inhibiting HRG-induced stimulation of ErbB2, ErbB3, and ErbB4. This inhibition is sufficient to effectively block HRG-stimulated cell growth. This novel ErbB3 receptor isoform, therefore, is disclosed as a potent modulator of HRG regulated cell proliferation and differentiation in normal human tissues, and an ideal candidate for the development of novel cancer therapeutics.

EXAMPLES AND PREFERRED EMBODIMENTS

Conditioned Media from Cells Expressing p45-sErbB3 and p85-sErbB3 Inhibit HRG Activation of ErbB3. p45-sErbB3 and p85-sErbB3 are naturally occurring secreted products of the ErbB3 gene (Lee and Maihle 1998). p45-sErbB3 contains the amino-terminal 310 amino acids of ErbB3 and two unique carboxy-terminal amino acid residues. p85-sErbB3 contains the amino-terminal 519 amino acids of ErbB3 and 24 unique carboxy-terminal amino acid residues (See FIG. 1). To examine whether p45-sErbB3 and p85-sErbB3 can modulate HRG receptor activation cells stably transfected with these corresponding cDNA clones were isolated. These cells secrete p45-sErbB3 and p85-sErbB3 into the culture medium (See FIG. 2A). The conditioned medium from these cells was used as the source of p45-sErbB3 or p85-sErbB3 in a series of preliminary experiments described below.

To test the ability of p45-sErbB3 and p85-sErbB3 to modulate aspects of HRG-mediated ErbB receptor activation a clonal derivative of the Ba/F3 cell line expressing exogenous ErbB2 and ErbB3 was stimulated with HRGβ EGF domain$_{177\text{-}241}$ (HRGα) and HRGβ1$_{1176}$-246 (HRGβ) in the absence or presence of concentrated conditioned media containing p45-sErbB3 and p85-sErbB3. As shown in FIG. 2, HRGβ was at least 20-fold more effective than HRGα in stimulating ErbB3 tyrosine phosphorylation. Conditioned media containing sErbB3 inhibited HRGα-stimulated ErbB3 activation by 40% (p45-sErbB3) and 80% (p85-sErbB3) at 1 μg/ml HRGA, as determined by densitometric analysis. However, at a higher concentration (2 μg/ml), conditioned media containing p85-sErbB3 decreased activation by 30%, although inhibition by conditioned media containing p45-sErbB3 was negligible (See FIG. 2A). In the presence of conditioned medium containing either p45-sErbB3 or p85-sErbB3, ligand stimulation of ErbB3 tyrosine phosphorylation was decreased by 60% and 90%, respectively, at both 50 and 100 ng/ml HRGβ (See FIG. 2C). These data indicate that p85-sErbB3 inhibited ErbB3 phosphorylation in response to both HRGα and HRGβ more effectively than p45-sErbB3, although the concentration of p85-sErbB3 used in these studies was lower than that of p45-sErbB3 (FIG. 2A).

Purification of p85-sErbB3. p85-sErbB3 was isolated from a concentrated conditioned medium of cells stably transfected with a cDNA clone R31 F encoding p85-sErbB3 (ref) and was purified in two steps. The first step was lectin affinity chromatography with a Con A column (Sigma). The bound p85-sErbB3 was washed with column buffer (10 mM Tris-HC1, pH 7.5, 150 mM NaC1, mM MnC1$_2$, and 1 mM CaC1$_2$) and eluted using column buffer containing 1 M αmethyl D-mannoside, then dialyzed against 20 mM Tris-HC1, pH 7.5 overnight. The second step of purification was accomplished using a MONO Q®, an ion exchanger for resolution of proteins and peptides ion exchange FPLC®, i.e., a microprocessor controlled, solvent delivery apparatus used in purification of biologically active compounds column (Pharmacia). The bound p85-sErbB3 was eluted from the column with 0-500 mM NaC1gradient containing 20 mM Tris-HC1, pH 7.5. Samples taken from each step were subjected to SDS-PAGE in duplicate and analyzed by Coomassie staining and by Western blot using anti-ErbB3 236 antibody recognizing the extracellular domain of the ErbB3 (Lee and Maihle 1998). The final p85-sErbB3 pool was homogeneous on SDS-PAGE, and the identity of the purified protein was confirmed by Western blot analysis. Purified preparations of p85-sErbB3 were used in all subsequent experiments.

p85-sErbB3 Binds to HRG with High Affinity. Previous reports based the assignation of the subdomain boundaries of the ErbB3 extracellular domain on the subdomain boundaries of EGFR (Lee and Maihle 1998) as defined by the genomic structure of avian ErbB1(Callaghan, Antczak et al. 1993). Accordingly, p85-sErbB3 is composed of subdomains I through III and includes the first 45 amino acids of subdomain IV (aa 1-519), and a unique twenty-four amino acid sequence at the carboxy-terminus. Binding studies using heregulins indicate that subdomains I and II are required for heregulin binding (Singer, Landgraf et al. 2001). On the other hand, for EGF binding to EGFR subdomains I and III are low and high affinity binding sites, respectively (Lax, Bellot et al. 1989).

Because p85-sErbB3 contains both subdomains I through III the present invention determined that p85-sErbB3 would bind to heregulins.

Direct binding between p85-sErbB3 and radiolabeled HRGβ was examined using the chemical crosslinker BS³. As shown in FIG. 3A, a protein complex of 90 kDa was formed between p85-sErbB3 and $^{125}$I-HRGβ. Formation of this complex could be inhibited by addition of excess cold HRGβ but not by addition of excess insulin, indicating that p85-sErbB3 binding to HRGβ is specific and that purified preparations of p85-sErbB3 are biologically active. An analysis of 125I-HRGβ$_{177-244}$ binding to immobilized p85-sErbB3 was then performed using an ErbB3-IgG homodimer as a positive control. As shown in FIG. 3, p85-sErbB3 binds to HRGβ$_{177-244}$ with a $K_D$ of 3.0±0.2 nM. In comparison, ErbB3-IgG binds to HRGβ$_{177-244}$ with a $K_D$ of 4.7±0.2 nM. These results demonstrate that p85-sErbB3 binds to HRGβ$_{177-244}$ with an affinity similar to that of the extracellular domain of ErbB3. Based on the results of these two complementary experimental approaches, the present invention establishes the use of p85-sErbB3 to bind to HRG with an affinity equivalent to the affinity of HRG for the full-length extracellular domain of ErbB3.

p85-sErbB3 Inhibits Binding of HRG to Receptors on the Cell Surface. The present invention also discloses the use of p85-sErbB3 to effectively limit binding of heregulin to cell surface receptors in the breast carcinoma cell line T47D. This cell line expresses all four ErbB receptors at moderate levels. Cells were incubated with varying concentrations of p85-sErbB3 in the presence of $^{125}$I-labeled HRGβ$_{177-244}$. Simultaneously, a separate group of cells was incubated with 125I-HRGβ$_{177-244}$ in the presence of varying concentrations of 2C4, a monoclonal antibody specific for the ErbB2 extracellular domain (Lewis, Lofgren et al. 1996). As shown by the inhibition curves (See FIG. 4), p85-sErbB3 and 2C4 inhibit HRGβ$_{177-244}$ binding to cell surface receptors with similar IC$_{50}$ values (0.45±0.03 nM and 0.55±0.03 nM, respectively) although the mechanism of inhibition by these two molecules is distinct. Although 2C4 inhibits heregulin binding to cell surface receptors by blocking ErbB2-ErbB3 heterodimerization via binding to the ErbB2 extracellular domain (Fitzpatrick, Pisacane et al. 1998), p85-sErbB3 inhibited receptor activation, at least in part, by competing for heregulin binding to the cell surface.

p85-sErbB3 Blocks HRG-Induced Activation of ErbB2, ErbB3, and ErbB4. The present invention also examined the ability of p85-sErbB3 to modulate HRG-stimulated receptor activation in the Ba/F3 (ErbB2+ErbB3) cell line using purified p85-sErbB3. This allowed an analysis of the mechanism of p85-sErbB3 mediated inhibition in a quantitative manner. As shown in FIG. 5, when Ba/F3 (ErbB2+ErbB3) cells were treated with p85-sErbB3 at a 10-fold molar excess over HRGβ$_{1-241}$, ErbB3 phosphorylation levels were reduced to basal levels. A similar level of receptor inhibition also was apparent when either a 2.5- or 5-fold molar excess of p85-sErbB3 was used in these experiments. Exogenous addition of p85-sErbB3 also inhibited HRG-induced ErbB2 activation. p85-sErbB3 blocked HRG stimulation whether the cells were treated with the EGF-like domain of HRG (HRGα or HRGβ), as shown in FIG. 2, or with HRGβ$_{1-241}$ (See FIG. 5), suggesting that inhibition by p85-sErbB3 occurs, at least in part, through a direct interaction between p85-sErbB3 and the EGF-like domain of HRG. Cells treated with the same concentration of p85-sErbB3 but not stimulated with HRG did not exhibit altered ErbB2 or ErbB3 tyrosine phosphorylation, or show any change in the level of either ErbB2 or ErbB3 expression, suggesting that p85-sErbB3 does not function as a "ligand" for these receptors.

To examine whether exogenous addition of p85-sErbB3 exerts the same inhibitory effect on endogenously expressed ErbB receptors, and to determine whether p85-sErbB3 could modulate other members of the EGF receptor family, the activity of p85-sErbB3 in two breast carcinoma cell lines, i.e., T47D and MCF7, was tested. As shown in FIG. 6A, addition of p85-sErbB3 (at a 6-fold molar excess relative to HRGβ) inhibited HRG-induced activation of ErbB2, ErbB3, and ErbB4 in both the T47D and MCF7 cell lines. In contrast, at least in these two cell lines which express low EGFR levels, EGFR phosphorylation remained at basal level in cells treated with HRGβ regardless of whether p85-sErbB3 was present or not. Similarly, EGF-induced phosphorylation of EGFR or ErbB2, or, to a lesser degree, phosphorylation of ErbB3, was not decreased by p85-sErbB3. These results demonstrate that inhibition by p85-sErbB3 is specific for HRG-induced activation of ErbB2, ErbB3, and ErbB4.

It is notable that in the T47D cells, a decrease in ErbB2, ErbB3, and ErbB4 protein levels following HRG stimulation was observed. In MCF7 cells a decrease in ErbB3 levels also was apparent when HRG was added to the culture medium (See FIG. 6A). It has been reported that the polyclonal ErbB3 antibody specific to the carboxy-terminal 17 aa used in this study preferentially recognizes non-phosphorylated ErbB3 on Western blots (Vartanian, Goodearl et al. 1997). Thus, when T47D or MCF7 cells are stimulated with HRG, a significant fraction of ErbB3 is phosphorylated, and, therefore, undetectable with this particular ErbB3 antibody. The anti-ErbB antibodies used in these experiments recognize the carboxy-terminal 17 aa (ErbB3) and 18 aa (ErbB2 and ErbB4) sequences of these receptors. Each of these sequences contains one tyrosine residue. Immunoblot detection by the anti-ErbB2 and ErbB4 antibodies used in this study, therefore, may reflect either the level of receptor expression or the unphosphorylated fraction of these receptors.

p85-sErbB3 Inhibits Activation of Downstream Effectors of HRG. HRG-stimulated activation of ErbB2, ErbB3, and ErbB4 leads to activation of two major signal transduction pathways: the PI3K pathway and the MAPK pathway (Wallasch, Weiss et al. 1995). The present invention tested whether p85-sErbB3 could inhibit activation of these two downstream effector pathways in T47D cells. Specifically, the present invention examined activation of MAPK and Akt by analyzing the phosphorylation levels of these proteins, and examined the ability of p85 phosphatidylinositide 3-kinase ("PI3K") to interact with ErbB3 following HRGβ treatment. In the presence of p85-sErbB3 (10-fold molar excess relative to HRGβ), tyrosine phosphorylation of ErbB3 was reduced to basal levels. In the same cell population, addition of exogenous p85-sErbB3 abrogated the phosphorylation of both MAPK and Akt as determined by Western blot analysis, and inhibited ErbB3's association with p85 PI3K (See FIG. 6B). These results further demonstrate that p85-sErbB3 can inhibit the activation of ErbB2, ErbB3, and ErbB4, and this inhibition affects the activation of downstream signaling molecules such as MAPK, Akt, and PI3K.

p85-sErbB3 Inhibits HRG-stimulated Cell Growth. The present invention also discloses the inhibition of HRG-induced phosphorylation of ErbB receptors by p85-sErbB3 as correlated with the modulation of HRG's biological effects. Specifically, a cell growth assay using MCF7 cells stimulated with HRGβ was performed and showed that, within the concentration range tested, growth of this cell line was dose-dependent (See FIG. 7). It was observed that at a concentration of 0.4 nM HRGβ the cell growth rate was half of the rate observed at saturating levels of HRGβ. In cell cultures grown in the presence of 0.4 nM HRGβ and p85-sErbB3 (a 100-fold molar excess relative to HRGβ), p85-sErbB3 inhibited cell growth by 75% and 90%, at densities of 5,000 and 8,000 cells/well, respectively, whereas the same concentration of p85-sErbB3 did not affect cell growth in the absence of HRGβ (See FIG. 7). Thus, the present invention discloses the use of p85-sErbB3 as a potent inhibitor of HRG-dependent breast carcinoma cell growth in vitro.

REFERENCES

Alimandi, M., M. Heidaran, et al. (1995). "Cooperative signaling of ErbB3 and ErbB2 in neoplastic transformation and human mammary carcinomas." *Oncogene* 10: 1813-1821.

Alroy, I. and Y. Yarden (1997). "The ErbB signaling network in embryogenesis and oncogenesis: signal diversification through combinatorial ligand-receptor interactions." *FEBS Lett.* 410(1): 83-86.

Basu, A., M. Raghunath, et al. (1989). "Inhibition of tyrosine kinase activity of the epidermal growth factor (EGF) receptor by a truncated receptor form that binds to EGF: role for interreceptor interaction in kinase regulation." *Mol. Cell. Biol.* 9(2): 671-677.

Callaghan, T., M. Antczak, et al. (1993). "A complete description of the EGF-receptor exon structure: implication in oncogenic activation and domain evolution." *Oncogene* 8: 2939-2948.

Carraway, K. L. I. and S. J. Burden (1995). "Neuregulins and their receptors." *Current Opinion in Neurobiology* 5: 606-612.

Doherty, J. K., C. Bond, et al. (1999). "The HER-2/neu receptor tyrosine kinase gene encodes a secreted autoinhibitor." *Proc. Natl. Acad. Sci. USA* 96(19): 10869-10874.

Falls, D. L., K. M. Rosen, et al. (1993). "ARIA, a protein that stimulates acetylcholine receptor synthesis, is a member of the neu ligand family." *Cell* 72(5): 801-15.

Fitzpatrick, V. D., P. I. Pisacane, et al. (1998). "Formation of a high affinity heregulin binding site using the soluble extracellular domains of ErbB2 with ErbB3 or ErbB4." *FEBS Lett.* 431(1): 102-106.

Flickinger, T. W., N. J. Maihle, et al. (1992). "An alternatively processed mRNA from the avian c-erbB gene encodes a soluble, truncated form of the receptor that can block ligand-dependent transformation." *Mol. Cell. Biol.* 12(2): 883-893.

Hijazi, M. M., E. W. Thompson, et al. (2000). "Heregulin regulates the actin cytoskeleton and promotes invasive properties in breast cancer cell lines." *International Journal of Oncology* 17(4): 629-41.

Holmes, W. E., M. X. Sliwkowski, et al. (1992). "Identification of heregulin, a specific activator of p185erbB2." *Science* 256(5060): 1205-1210.

Katoh, M., Y. Yazaki, et al. (1993). "c-erbB3 gene encodes secreted as well as transmembrane receptor tyrosine kinase." *Biochem. Biophys. Res. Commun.* 192(3): 1189-1197.

Krane, I. M. and P. Leder (1996). "NDF/heregulin induces persistence of terminal end buds and adenocarcinomas in the mammary glands of transgenic mice." *Oncogene* 12(8): 1781-1788.

Kraus, M. H., W. Issing, et al. (1989). "Isolation and characterization of ERBB3, a third member of the ERBB/epidermal growth factor receptor family: evidence for overexpression in a subset of human mammary tumors." *Proc. Natl. Acad. Sci. USA* 86: 9193-9197.

Lax, I., F. Bellot, et al. (1989). "Functional analysis of the ligand binding site of EGF-receptor utilizing chimeric chicken/human receptor molecules." *EMBO J.* 8(2): 421-427.

Lee, H. and N. J. Maihle (1998). "Isolation and characterization of four alternate c-erbB3 transcripts expressed in ovarian carcinoma-derived cell lines and normal human tissues." *Oncogene* 16(25): 3243-3252.

Lewis, G. D., J. A. Lofgren, et al. (1996). "Growth regulation of human breast and ovarian tumor cells by heregulin: Evidence for the requirement of ErbB2 as a critical component in mediating heregulin responsiveness." *Cancer Res.* 56(6): 1457-1465.

Marchionni, M. A., A. D. Goodearl, et al. (1993). "Glial growth factors are alternatively spliced erbB2 ligands expressed in the nervous system." *Nature* 362(6418): 312-8.

Meyer, D. and C. Birchmeier (1995). "Multiple essential functions of neuregulin in development [see comments] [published erratum appears in Nature Dec. 14, 1995;378 (6558):753 ]." *Nature* 378(6555): 386-390.

Peles, E., S. S. Bacus, et al. (1992). "Isolation of the neu/HER-2 stimulatory ligand: a 44 kd glycoprotein that induces differentiation of mammary tumor cells." *Cell* 69(1): 205-16.

Plowman, G. D., J. M. Culouscou, et al. (1993). "Ligand-specific activation of HER4/p180erbB4, a fourth member of the epidermal growth factor receptor family." *Proc. Natl. Acad. Sci. USA* 90(5): 1746-1750.

Plowman, G. D., G. S. Whitney, et al. (1990). "Molecular cloning and expression of an additional epidermal growth factor receptor-related gene." *Proc. Natl. Acad. Sci. USA* 87(13): 4905-4909.

Ram, T. G., M. E. Schelling, et al. (2000). "Blocking HER-2/HER-3 function with a dominant negative form of HER-3 in cells stimulated by heregulin and in breast cancer cells with HER-2 gene amplification." *Cell Growth Differ.* 11(3): 173-183.

Redemann, N., B. Holzmann, et al. (1992). "Anti-oncogenic activity of signalling-defective epidermal growth factor receptor mutants." *Mol. Cell. Biol.* 12(2): 491-498.

Robinson, D., F. He, et al. (1996). "A tyrosine kinase profile of prostate carcinoma." *Proc. Nati. Acad. Sci. USA* 93(12): 5958-5962.

Siegel, P. M., E. D. Ryan, et al. (1999). "Elevated expression of activated forms of Neu/ErbB-2 and ErbB-3 are involved in the induction of mammary tumors in transgenic mice: implications for human breast cancer." *EMBO Journal* 18(8): 2149-2164.

Singer, E., R. Landgraf, et al. (2001). "Identification of a heregulin binding site in HER3 extracellular domain." *Journal of Biological Chemistry* 276(47): 44266-74.

Sundaresan, S., E. Penuel, et al. (1999). "The biology of human epidermal growth factor receptor 2." *Curr. Oncol. Report* 1: 16-22.

Tsai, M. S:, A. E. Hornby, et al. (2000). "Expression and function of CYR61, an angiogenic factor, in breast cancer cell lines and tumor biopsies." *Cancer Research* 60(20): 5603-7.

Vartanian, T., A. Goodearl, et al. (1997). "Axonal Neuregulin Signals Cells of the Oligodendrocyte Lineage though Activation of HER4 and Schwann Cells though HER2 and HER3." *J. Cell Biol.* 137: 211.

Wallasch, C., F. U. Weiss, et al. (1995). "Heregulin-dependent regulation of HER2/neu oncogenic signaling by heterodimerization with HER3." *EMBO J.* 14(17): 4267-4275.

Wen, D., E. Peles, et al. (1992). "Neu differentiation factor: a transmembrane glycoprotein containing an EGF domain and an immunoglobulin homology unit." *Cell* 69(3): 559-72.

p85-sErbB3 protein (1) Information for SEQ ID NO:2:
  (i) Sequence characteristics:
  (ii) Length
  (iii) Type
  (iv) Molecule type
  (v) Original source:
  (vi) Organism: homo sapience (2) Information for SEQ ID NO:3:
  (i) Sequence characteristics:
  (ii) Length
  (iii) Type
  (iv) Molecule type
  (v) Original source:
  (vi) Organism: homo sapience (3) Information for SEQ ID NO:4:
  (i) Sequence characteristics:
  (ii) Length
  (iii) Type
  (iv) Molecule type
  (v) Original source:
  (vi) Organism: homo sapience tested, growth of this cell line was dose-dependent (See FIG. 7). It was observed that at a concentration of 0.4 nM HRGβ the cell growth rate was half of the rate observed at saturating levels of HRGβ. In cell cultures grown in the presence of 0.4 nM HRGβ and p85-sErbB3 (a 100-fold molar excess relative to HRGβ), p85-sErbB3 inhibited cell growth by 75% and 90%, at densities of 5,000 and 8,000 cells/well, respectively, whereas the same concentration of p85-sErbB3 did not affect cell growth in the absence of HRGβ (See FIG. 7). Thus, the present invention discloses the use of p85-sErbB3 as a potent inhibitor of HRG-dependent breast carcinoma cell growth in vitro.

We claim:

1. An expression vector encoding an isoform of human ErbB3, wherein said isoform consists of SEQ ID NO: 2 or SEQ ID NO: 4.

2. A host cell comprising an expression vector of claim 1.

3. A method of producing a soluble receptor, comprising:
   a. culturing a cell of claim 2 under conditions in which proteins are expressed; and
   b. harvesting said proteins.

4. An isolated nucleic acid selected from the group consisting of: a) a nucleic acid sequence consisting of SEQ ID NO. 1 or SEQ ID NO. 3; and b) a nucleic acid sequence encoding the protein consisting of SEQ ID NO: 2 or SEQ ID NO: 4, wherein said protein binds heregulins and has the ability to elicit an immune response.

5. The isolated nucleic acid of claim 4, wherein the nucleic acid consists of SEQ ID NO: 1 or SEQ ID NO: 3.

6. The isolated nucleic acid of claim 4 wherein the nucleic acid encodes a protein consisting of the amino acid sequence SEQ ID NO. 2 or SEQ ID NO: 4.

7. An isolated nucleic acid sequence which is at least 99% identical to SEQ ID NO: 1.

* * * * *

SEQUENCE LISTING

```
<160> NUMBER OF SEQ ID NOS: 8

<210> SEQ ID NO 1
<211> LENGTH: 1800
<212> TYPE: DNA
<213> ORGANISM: Homo sapiens
<220> FEATURE:
<221> NAME/KEY: CDS
<222> LOCATION: (61)..(1746)

<400> SEQUENCE: 1 cgggccccccc ctcgaggtcg ggccggactt ggctgggctc ccttcacccct ctgcggagtc      60 atg agg gcg aac gac gct ctg cag gtg ctg ggc ttg ctt ttc agc ctg        108
Met Arg Ala Asn Asp Ala Leu Gln Val Leu Gly Leu Leu Phe Ser Leu
1               5                   10                  15 gcc cgg ggc tcc gag gtg ggc aac tct cag gca gtg tgt cct ggg act        156
Ala Arg Gly Ser Glu Val Gly Asn Ser Gln Ala Val Cys Pro Gly Thr
            20                  25                  30 ctg aat ggc ctg agt gtg acc ggc gat gct gag aac caa tac cag aca        204
Leu Asn Gly Leu Ser Val Thr Gly Asp Ala Glu Asn Gln Tyr Gln Thr
        35                  40                  45 ctg tac aag ctc tac gag agg tgt gag gtg gtg atg ggg aac ctt gag        252
Leu Tyr Lys Leu Tyr Glu Arg Cys Glu Val Val Met Gly Asn Leu Glu
    50                  55                  60 att gtg ctc acg gga cac aat gcc gac ctc tcc ttc ctg cag tgg att        300
Ile Val Leu Thr Gly His Asn Ala Asp Leu Ser Phe Leu Gln Trp Ile
65                  70                  75                  80 cga gaa gtg aca ggc tat gtc ctc gtg gcc atg aat gaa ttc tct act        348
Arg Glu Val Thr Gly Tyr Val Leu Val Ala Met Asn Glu Phe Ser Thr
                85                  90                  95 cta cca ttg ccc aac ctc cgc gtg gtg cga ggg acc cag gtc tac gat        396
Leu Pro Leu Pro Asn Leu Arg Val Val Arg Gly Thr Gln Val Tyr Asp
            100                 105                 110 ggg aag ttt gcc atc ttc gtc atg ttg aac tat aac acc aac tcc agc        444
Gly Lys Phe Ala Ile Phe Val Met Leu Asn Tyr Asn Thr Asn Ser Ser
        115                 120                 125 cac gct ctg cgc cag ctc cgc ttg act cag ctc acc gag att ctg tca        492
```

```
                          -continued

His Ala Leu Arg Gln Leu Arg Leu Thr Gln Leu Thr Glu Ile Leu Ser
    130                 135                 140 ggg ggt gtt tat att gag aag aac gat aag ctt tgt cac atg gac aca    540
Gly Gly Val Tyr Ile Glu Lys Asn Asp Lys Leu Cys His Met Asp Thr
145                 150                 155                 160 att gac tgg agg gac atc gtg agg gac cga gat gct gag ata gtg gtg    588
Ile Asp Trp Arg Asp Ile Val Arg Asp Arg Asp Ala Glu Ile Val Val
                165                 170                 175 aag gac aat ggc aga agc tgt ccc ccc tgt cat gag gtt tgc aag ggg    636
Lys Asp Asn Gly Arg Ser Cys Pro Pro Cys His Glu Val Cys Lys Gly
            180                 185                 190 cga tgc tgg ggt cct gga tca gaa gac tgc cag aca ttg acc aag acc    684
Arg Cys Trp Gly Pro Gly Ser Glu Asp Cys Gln Thr Leu Thr Lys Thr
        195                 200                 205 atc tgt gct cct cag tgt aat ggt cac tgc ttt ggg ccc aac ccc aac    732
Ile Cys Ala Pro Gln Cys Asn Gly His Cys Phe Gly Pro Asn Pro Asn
210                 215                 220 cag tgc tgc cat gat gag tgt gcc ggg ggc tgc tca ggc cct cag gac    780
Gln Cys Cys His Asp Glu Cys Ala Gly Gly Cys Ser Gly Pro Gln Asp
225                 230                 235                 240 aca gac tgc ttt gcc tgc cgg cac ttc aat gac agt gga gcc tgt gta    828
Thr Asp Cys Phe Ala Cys Arg His Phe Asn Asp Ser Gly Ala Cys Val
                245                 250                 255 cct cgc tgt cca cag cct ctt gtc tac aac aag cta act ttc cag ctg    876
Pro Arg Cys Pro Gln Pro Leu Val Tyr Asn Lys Leu Thr Phe Gln Leu
            260                 265                 270 gaa ccc aat ccc cac acc aag tat cag tat gga gga gtt tgt gta gcc    924
Glu Pro Asn Pro His Thr Lys Tyr Gln Tyr Gly Gly Val Cys Val Ala
        275                 280                 285 agc tgt ccc cat aac ttt gtg gtg gat caa aca tcc tgt gtc agg gcc    972
Ser Cys Pro His Asn Phe Val Val Asp Gln Thr Ser Cys Val Arg Ala
290                 295                 300 tgt cct cct gac aag atg gaa gta gat aaa aat ggg ctc aag atg tgt   1020
Cys Pro Pro Asp Lys Met Glu Val Asp Lys Asn Gly Leu Lys Met Cys
305                 310                 315                 320 gag cct tgt ggg gga cta tgt ccc aaa gcc tgt gag gga aca ggc tct   1068
Glu Pro Cys Gly Gly Leu Cys Pro Lys Ala Cys Glu Gly Thr Gly Ser
                325                 330                 335 ggg agc cgc ttc cag act gtg gac tcg agc aac att gat gga ttt gtg   1116
Gly Ser Arg Phe Gln Thr Val Asp Ser Ser Asn Ile Asp Gly Phe Val
            340                 345                 350 aac tgc acc aag atc ctg ggc aac ctg gac ttt ctg atc acc ggc ctc   1164
Asn Cys Thr Lys Ile Leu Gly Asn Leu Asp Phe Leu Ile Thr Gly Leu
        355                 360                 365 aat gga gac ccc tgg cac aag atc cct gcc ctg gac cca gag aag ctc   1212
Asn Gly Asp Pro Trp His Lys Ile Pro Ala Leu Asp Pro Glu Lys Leu
370                 375                 380 aat gtc ttc cgg aca gta cgg gag atc aca ggt tac ctg aac atc cag   1260
Asn Val Phe Arg Thr Val Arg Glu Ile Thr Gly Tyr Leu Asn Ile Gln
385                 390                 395                 400 tcc tgg ccg ccc cac atg cac aac ttc agt gtt ttt tcc aat ttg aca   1308
Ser Trp Pro Pro His Met His Asn Phe Ser Val Phe Ser Asn Leu Thr
                405                 410                 415 acc att gga ggc aga agc ctc tac aac cgg ggc ttc tca ttg ttg atc   1356
Thr Ile Gly Gly Arg Ser Leu Tyr Asn Arg Gly Phe Ser Leu Leu Ile
            420                 425                 430 atg aag aac ttg aat gtc aca tct ctg ggc ttc cga tcc ctg aag gaa   1404
Met Lys Asn Leu Asn Val Thr Ser Leu Gly Phe Arg Ser Leu Lys Glu
        435                 440                 445
```

-continued

```
att agt gct ggg cgt atc tat ata agt gcc aat agg cag ctc tgc tac    1452
Ile Ser Ala Gly Arg Ile Tyr Ile Ser Ala Asn Arg Gln Leu Cys Tyr
    450                 455                 460 cac cac tct ttg aac tgg acc aag gtg ctt cgg ggg cct acg gaa gag    1500
His His Ser Leu Asn Trp Thr Lys Val Leu Arg Gly Pro Thr Glu Glu
465                 470                 475                 480 cga cta gac atc aag cat aat cgg ccg cgc aga gac tgc gtg gca gag    1548
Arg Leu Asp Ile Lys His Asn Arg Pro Arg Arg Asp Cys Val Ala Glu
                    485                 490                 495 ggc aaa gtg tgt gac cca ctg tgc tcc tct ggg gga tgc tgg ggc cca    1596
Gly Lys Val Cys Asp Pro Leu Cys Ser Ser Gly Gly Cys Trp Gly Pro
                500                 505                 510 ggc cct ggt cag tgc ttg tcc tgt cga aat tat agc cga gga ggt gtc    1644
Gly Pro Gly Gln Cys Leu Ser Cys Arg Asn Tyr Ser Arg Gly Gly Val
            515                 520                 525 tgt gtg acc cac tgc aac ttt ttg aat ggg tac agt aag ggg agc cag    1692
Cys Val Thr His Cys Asn Phe Leu Asn Gly Tyr Ser Lys Gly Ser Gln
530                 535                 540 tca agg atg ggt ggg ggt ggg gcc ctg caa tgg aac tgt tca ggt ggc    1740
Ser Arg Met Gly Gly Gly Gly Ala Leu Gln Trp Asn Cys Ser Gly Gly
545                 550                 555                 560 ata caa taaaagtctt tagacaaaaa aaaaaaaaaa aaaaaaaaaa aaaaaaaaaa    1796
Ile Gln aaaa                                                               1800

<210> SEQ ID NO 2
<211> LENGTH: 562
<212> TYPE: PRT
<213> ORGANISM: Homo sapiens

<400> SEQUENCE: 2

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
        50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205
```

```
Ile Cys Ala Pro Gln Cys Asn Gly His Cys Phe Gly Pro Asn Pro Asn
    210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
        275                 280                 285
Ser Cys Pro His Asn Phe Val Val Asp Gln Thr Ser Cys Val Arg Ala
    290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
                340                 345                 350
Asn Cys Thr Lys Ile Leu Gly Asn Leu Asp Phe Leu Ile Thr Gly Leu
        355                 360                 365
Asn Gly Asp Pro Trp His Lys Ile Pro Ala Leu Asp Pro Glu Lys Leu
    370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
                420                 425                 430
Met Lys Asn Leu Asn Val Thr Ser Leu Gly Phe Arg Ser Leu Lys Glu
        435                 440                 445
Ile Ser Ala Gly Arg Ile Tyr Ile Ser Ala Asn Arg Gln Leu Cys Tyr
    450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Ser Gly Gly Cys Trp Gly Pro
            500                 505                 510
Gly Pro Gly Gln Cys Leu Ser Cys Arg Asn Tyr Ser Arg Gly Gly Val
        515                 520                 525
Cys Val Thr His Cys Asn Phe Leu Asn Gly Tyr Ser Lys Gly Ser Gln
    530                 535                 540
Ser Arg Met Gly Gly Gly Gly Ala Leu Gln Trp Asn Cys Ser Gly Gly
545                 550                 555                 560
Ile Gln

<210> SEQ ID NO 3
<211> LENGTH: 1420
<212> TYPE: DNA
<213> ORGANISM: Homo sapiens
<220> FEATURE:
<221> NAME/KEY: CDS
<222> LOCATION: (61)..(1053)

<400> SEQUENCE: 3
```

-continued

| | |
|---|---|
| cgggccccccc ctcgaggtcg ggccggactt ggctgggctc ccttcaccct ctgcggagtc | 60 |
| atg agg gcg aac gac gct ctg cag gtg ctg ggc ttg ctt ttc agc ctg<br>Met Arg Ala Asn Asp Ala Leu Gln Val Leu Gly Leu Leu Phe Ser Leu<br>1                         5                    10                  15 | 108 |
| gcc cgg ggc tcc gag gtg ggc aac tct cag gca gtg tgt cct ggg act<br>Ala Arg Gly Ser Glu Val Gly Asn Ser Gln Ala Val Cys Pro Gly Thr<br>           20                    25                    30 | 156 |
| ctg aat ggc ctg agt gtg acc ggc gat gct gag aac caa tac cag aca<br>Leu Asn Gly Leu Ser Val Thr Gly Asp Ala Glu Asn Gln Tyr Gln Thr<br>                 35                    40                    45 | 204 |
| ctg tac aag ctc tac gag agg tgt gag gtg gtg atg ggg aac ctt gag<br>Leu Tyr Lys Leu Tyr Glu Arg Cys Glu Val Val Met Gly Asn Leu Glu<br> 50                         55                    60 | 252 |
| att gtg ctc acg gga cac aat gcc gac ctc tcc ttc ctg cag tgg att<br>Ile Val Leu Thr Gly His Asn Ala Asp Leu Ser Phe Leu Gln Trp Ile<br> 65                         70                    75                  80 | 300 |
| cga gaa gtg aca ggc tat gtc ctc gtg gcc atg aat gaa ttc tct act<br>Arg Glu Val Thr Gly Tyr Val Leu Val Ala Met Asn Glu Phe Ser Thr<br>                       85                    90                    95 | 348 |
| cta cca ttg ccc aac ctc cgc gtg gtg cga ggg acc cag gtc tac gat<br>Leu Pro Leu Pro Asn Leu Arg Val Val Arg Gly Thr Gln Val Tyr Asp<br>          100                    105                   110 | 396 |
| ggg aag ttt gcc atc ttc gtc atg ttg aac tat aac acc aac tcc agc<br>Gly Lys Phe Ala Ile Phe Val Met Leu Asn Tyr Asn Thr Asn Ser Ser<br>               115                    120                   125 | 444 |
| cac gct ctg cgc cag ctc cgc ttg act cag ctc acc gag att ctg tca<br>His Ala Leu Arg Gln Leu Arg Leu Thr Gln Leu Thr Glu Ile Leu Ser<br>130                       135                    140 | 492 |
| ggg ggt gtt tat att gag aag aac gat aag ctt tgt cac atg gac aca<br>Gly Gly Val Tyr Ile Glu Lys Asn Asp Lys Leu Cys His Met Asp Thr<br>145                       150                    155                  160 | 540 |
| att gac tgg agg gac atc gtg agg gac cga gat gct gag ata gtg gtg<br>Ile Asp Trp Arg Asp Ile Val Arg Asp Arg Asp Ala Glu Ile Val Val<br>               165                    170                   175 | 588 |
| aag gac aat ggc aga agc tgt ccc ccc tgt cat gag gtt tgc aag ggg<br>Lys Asp Asn Gly Arg Ser Cys Pro Pro Cys His Glu Val Cys Lys Gly<br>180                       185                    190 | 636 |
| cga tgc tgg ggt cct gga tca gaa gac tgc cag aca ttg acc aag acc<br>Arg Cys Trp Gly Pro Gly Ser Glu Asp Cys Gln Thr Leu Thr Lys Thr<br>               195                    200                   205 | 684 |
| atc tgt gct cct cag tgt aat ggt cac tgc ttt ggg ccc aac ccc aac<br>Ile Cys Ala Pro Gln Cys Asn Gly His Cys Phe Gly Pro Asn Pro Asn<br>210                       215                    220 | 732 |
| cag tgc tgc cat gat gag tgt gcc ggg ggc tgc tca ggc cct cag gac<br>Gln Cys Cys His Asp Glu Cys Ala Gly Gly Cys Ser Gly Pro Gln Asp<br>225                       230                    235                  240 | 780 |
| aca gac tgc ttt gcc tgc cgg cac ttc aat gac agt gga gcc tgt gta<br>Thr Asp Cys Phe Ala Cys Arg His Phe Asn Asp Ser Gly Ala Cys Val<br>               245                    250                   255 | 828 |
| cct cgc tgt cca cag cct ctt gtc tac aac aag cta act ttc cag ctg<br>Pro Arg Cys Pro Gln Pro Leu Val Tyr Asn Lys Leu Thr Phe Gln Leu<br>          260                    265                   270 | 876 |
| gaa ccc aat ccc cac acc aag tat cag tat gga gga gtt tgt gta gcc<br>Glu Pro Asn Pro His Thr Lys Tyr Gln Tyr Gly Gly Val Cys Val Ala<br>               275                    280                   285 | 924 |
| agc tgt ccc cat aac ttt gtg gtg gat caa aca tcc tgt gtc agg gcc<br>Ser Cys Pro His Asn Phe Val Val Asp Gln Thr Ser Cys Val Arg Ala<br>290                       295                    300 | 972 |

-continued

```
tgt cct cct gac aag atg gaa gta gat aaa aat ggg ctc aag atg tgt    1020
Cys Pro Pro Asp Lys Met Glu Val Asp Lys Asn Gly Leu Lys Met Cys
305                 310                 315                 320 gag cct tgt ggg gga cta tgt ccc aaa ggt ggg taggagatgg taagaagttg    1073
Glu Pro Cys Gly Gly Leu Cys Pro Lys Gly Gly
                325                 330 taaagagaca gcctttcctc tgagcctgcg cagaccaccc ccactgaacc tctcttacat    1133
ttgcagcctg tgagggaaca ggctctggga gccgcttcca gactgtggac tcgagcaaca    1193
ttgatggatt tgtgaactgc accaagatcc tgggcaacct ggactttctg atcaccggcc    1253
tcaatgggtt agagatcctg ccttccctcc ttagacccca gcccacgcac ccctcacagt    1313
tcatttcatt ggccaaaact ttcctatgtg gagctgacta ggaatcaaag tcataaaatt    1373
ctagcctgtt acaaggaaa aaaaaaaaaa aaaaaaaaa aaaaaaa                    1420
```

<210> SEQ ID NO 4
<211> LENGTH: 331
<212> TYPE: PRT
<213> ORGANISM: Homo sapiens

<400> SEQUENCE: 4

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270
```

```
Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
        290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Gly Gly
                325                 330

<210> SEQ ID NO 5
<211> LENGTH: 2005
<212> TYPE: DNA
<213> ORGANISM: Homo sapiens
<220> FEATURE:
<221> NAME/KEY: CDS
<222> LOCATION: (61)..(1662)

<400> SEQUENCE: 5
```

| | |
|---|---:|
| cgggccccccc ctcgaggtcg ggccggactt ggctgggctc ccttcaccct ctgcggagtc | 60 |
| atg agg gcg aac gac gct ctg cag gtg ctg ggc ttg ctt ttc agc ctg<br>Met Arg Ala Asn Asp Ala Leu Gln Val Leu Gly Leu Leu Phe Ser Leu<br>1               5                  10                  15 | 108 |
| gcc cgg ggc tcc gag gtg ggc aac tct cag gca gtg tgt cct ggg act<br>Ala Arg Gly Ser Glu Val Gly Asn Ser Gln Ala Val Cys Pro Gly Thr<br>            20                  25                  30 | 156 |
| ctg aat ggc ctg agt gtg acc ggc gat gct gag aac caa tac cag aca<br>Leu Asn Gly Leu Ser Val Thr Gly Asp Ala Glu Asn Gln Tyr Gln Thr<br>        35                  40                  45 | 204 |
| ctg tac aag ctc tac gag agg tgt gag gtg gtg atg ggg aac ctt gag<br>Leu Tyr Lys Leu Tyr Glu Arg Cys Glu Val Val Met Gly Asn Leu Glu<br>    50                  55                  60 | 252 |
| att gtg ctc acg gga cac aat gcc gac ctc tcc ttc ctg cag tgg att<br>Ile Val Leu Thr Gly His Asn Ala Asp Leu Ser Phe Leu Gln Trp Ile<br>65                  70                  75                  80 | 300 |
| cga gaa gtg aca ggc tat gtc ctc gtg gcc atg aat gaa ttc tct act<br>Arg Glu Val Thr Gly Tyr Val Leu Val Ala Met Asn Glu Phe Ser Thr<br>                85                  90                  95 | 348 |
| cta cca ttg ccc aac ctc cgc gtg gtg cga ggg acc cag gtc tac gat<br>Leu Pro Leu Pro Asn Leu Arg Val Val Arg Gly Thr Gln Val Tyr Asp<br>            100                 105                 110 | 396 |
| ggg aag ttt gcc atc ttc gtc atg ttg aac tat aac acc aac tcc agc<br>Gly Lys Phe Ala Ile Phe Val Met Leu Asn Tyr Asn Thr Asn Ser Ser<br>        115                 120                 125 | 444 |
| cac gct ctg cgc cag ctc cgc ttg act cag ctc acc gag att ctg tca<br>His Ala Leu Arg Gln Leu Arg Leu Thr Gln Leu Thr Glu Ile Leu Ser<br>    130                 135                 140 | 492 |
| ggg ggt gtt tat att gag aag aac gat aag ctt tgt cac atg gac aca<br>Gly Gly Val Tyr Ile Glu Lys Asn Asp Lys Leu Cys His Met Asp Thr<br>145                 150                 155                 160 | 540 |
| att gac tgg agg gac atc gtg agg gac cga gat gct gag ata gtg gtg<br>Ile Asp Trp Arg Asp Ile Val Arg Asp Arg Asp Ala Glu Ile Val Val<br>                165                 170                 175 | 588 |
| aag gac aat ggc aga agc tgt ccc ccc tgt cat gag gtt tgc aag ggg<br>Lys Asp Asn Gly Arg Ser Cys Pro Pro Cys His Glu Val Cys Lys Gly<br>            180                 185                 190 | 636 |
| cga tgc tgg ggt cct gga tca gaa gac tgc cag aca ttg acc aag acc<br>Arg Cys Trp Gly Pro Gly Ser Glu Asp Cys Gln Thr Leu Thr Lys Thr<br>        195                 200                 205 | 684 |
| atc tgt gct cct cag tgt aat ggt cac tgc ttt ggg ccc aac ccc aac<br>Ile Cys Ala Pro Gln Cys Asn Gly His Cys Phe Gly Pro Asn Pro Asn | 732 |

-continued

|  |  |  |  |  |  |  |  |  |  |  |  |  |  |  |  |
|---|---|---|---|---|---|---|---|---|---|---|---|---|---|---|---|
|  |  | 210 |  |  |  | 215 |  |  |  | 220 |  |  |  |  |  |
| cag | tgc | tgc | cat | gat | gag | tgt | gcc | ggg | ggc | tgc | tca | ggc | cct | cag | gac | 780 |
| Gln | Cys | Cys | His | Asp | Glu | Cys | Ala | Gly | Gly | Cys | Ser | Gly | Pro | Gln | Asp |
| 225 |  |  |  | 230 |  |  |  |  | 235 |  |  |  |  | 240 |  |

| aca | gac | tgc | ttt | gcc | tgc | cgg | cac | ttc | aat | gac | agt | gga | gcc | tgt | gta | 828 |
| Thr | Asp | Cys | Phe | Ala | Cys | Arg | His | Phe | Asn | Asp | Ser | Gly | Ala | Cys | Val |
|  |  |  |  | 245 |  |  |  |  | 250 |  |  |  |  | 255 |  |

| cct | cgc | tgt | cca | cag | cct | ctt | gtc | tac | aac | aag | cta | act | ttc | cag | ctg | 876 |
| Pro | Arg | Cys | Pro | Gln | Pro | Leu | Val | Tyr | Asn | Lys | Leu | Thr | Phe | Gln | Leu |
|  |  | 260 |  |  |  |  | 265 |  |  |  |  | 270 |  |  |  |

| gaa | ccc | aat | ccc | cac | acc | aag | tat | cag | tat | gga | gga | gtt | tgt | gta | gcc | 924 |
| Glu | Pro | Asn | Pro | His | Thr | Lys | Tyr | Gln | Tyr | Gly | Gly | Val | Cys | Val | Ala |
| 275 |  |  |  |  | 280 |  |  |  |  | 285 |  |  |  |  |  |

| agc | tgt | ccc | cat | aac | ttt | gtg | gtg | gat | caa | aca | tcc | tgt | gtc | agg | gcc | 972 |
| Ser | Cys | Pro | His | Asn | Phe | Val | Val | Asp | Gln | Thr | Ser | Cys | Val | Arg | Ala |
|  | 290 |  |  |  |  | 295 |  |  |  |  | 300 |  |  |  |  |

| tgt | cct | cct | gac | aag | atg | gaa | gta | gat | aaa | aat | ggg | ctc | aag | atg | tgt | 1020 |
| Cys | Pro | Pro | Asp | Lys | Met | Glu | Val | Asp | Lys | Asn | Gly | Leu | Lys | Met | Cys |
| 305 |  |  |  |  | 310 |  |  |  |  | 315 |  |  |  |  | 320 |

| gag | cct | tgt | ggg | gga | cta | tgt | ccc | aaa | gcc | tgt | gag | gga | aca | ggc | tct | 1068 |
| Glu | Pro | Cys | Gly | Gly | Leu | Cys | Pro | Lys | Ala | Cys | Glu | Gly | Thr | Gly | Ser |
|  |  |  |  | 325 |  |  |  |  | 330 |  |  |  |  | 335 |  |

| ggg | agc | cgc | ttc | cag | act | gtg | gac | tcg | agc | aac | att | gat | gga | ttt | gtg | 1116 |
| Gly | Ser | Arg | Phe | Gln | Thr | Val | Asp | Ser | Ser | Asn | Ile | Asp | Gly | Phe | Val |
|  |  |  | 340 |  |  |  |  | 345 |  |  |  |  | 350 |  |  |

| aac | tgc | acc | aag | atc | ctg | ggc | aac | ctg | gac | ttt | ctg | atc | acc | ggc | ctc | 1164 |
| Asn | Cys | Thr | Lys | Ile | Leu | Gly | Asn | Leu | Asp | Phe | Leu | Ile | Thr | Gly | Leu |
|  |  | 355 |  |  |  |  | 360 |  |  |  |  | 365 |  |  |  |

| aat | gga | gac | ccc | tgg | cac | aag | atc | cct | gcc | ctg | gac | cca | gag | aag | ctc | 1212 |
| Asn | Gly | Asp | Pro | Trp | His | Lys | Ile | Pro | Ala | Leu | Asp | Pro | Glu | Lys | Leu |
| 370 |  |  |  |  | 375 |  |  |  |  | 380 |  |  |  |  |  |

| aat | gtc | ttc | cgg | aca | gta | cgg | gag | atc | aca | ggt | tac | ctg | aac | atc | cag | 1260 |
| Asn | Val | Phe | Arg | Thr | Val | Arg | Glu | Ile | Thr | Gly | Tyr | Leu | Asn | Ile | Gln |
| 385 |  |  |  | 390 |  |  |  |  | 395 |  |  |  |  | 400 |  |

| tcc | tgg | ccg | ccc | cac | atg | cac | aac | ttc | agt | gtt | ttt | tcc | aat | ttg | aca | 1308 |
| Ser | Trp | Pro | Pro | His | Met | His | Asn | Phe | Ser | Val | Phe | Ser | Asn | Leu | Thr |
|  |  |  |  | 405 |  |  |  |  | 410 |  |  |  |  | 415 |  |

| acc | att | gga | ggc | aga | agc | ctc | tac | aac | cgg | ggc | ttc | tca | ttg | ttg | atc | 1356 |
| Thr | Ile | Gly | Gly | Arg | Ser | Leu | Tyr | Asn | Arg | Gly | Phe | Ser | Leu | Leu | Ile |
|  |  |  | 420 |  |  |  |  | 425 |  |  |  |  | 430 |  |  |

| atg | aag | aac | ttg | aat | gtc | aca | tct | ctg | ggc | ttc | cga | tcc | ctg | aag | gaa | 1404 |
| Met | Lys | Asn | Leu | Asn | Val | Thr | Ser | Leu | Gly | Phe | Arg | Ser | Leu | Lys | Glu |
|  |  | 435 |  |  |  |  | 440 |  |  |  |  | 445 |  |  |  |

| att | agt | gct | ggg | cgt | atc | tat | ata | agt | gcc | aat | agg | cag | ctc | tgc | tac | 1452 |
| Ile | Ser | Ala | Gly | Arg | Ile | Tyr | Ile | Ser | Ala | Asn | Arg | Gln | Leu | Cys | Tyr |
| 450 |  |  |  |  | 455 |  |  |  |  | 460 |  |  |  |  |  |

| cac | cac | tct | ttg | aac | tgg | acc | aag | gtg | ctt | cgg | ggg | cct | acg | gaa | gag | 1500 |
| His | His | Ser | Leu | Asn | Trp | Thr | Lys | Val | Leu | Arg | Gly | Pro | Thr | Glu | Glu |
| 465 |  |  |  |  | 470 |  |  |  |  | 475 |  |  |  |  | 480 |

| cga | cta | gac | atc | aag | cat | aat | cgg | ccg | cgc | aga | gac | tgc | ggt | gag | gga | 1548 |
| Arg | Leu | Asp | Ile | Lys | His | Asn | Arg | Pro | Arg | Arg | Asp | Cys | Gly | Glu | Gly |
|  |  |  |  | 485 |  |  |  |  | 490 |  |  |  |  | 495 |  |

| aag | ggt | ctg | cta | ggt | ggt | gag | aat | agg | gag | tca | ggg | agg | aga | ggg | ctg | 1596 |
| Lys | Gly | Leu | Leu | Gly | Gly | Glu | Asn | Arg | Glu | Ser | Gly | Arg | Arg | Gly | Leu |
|  |  |  | 500 |  |  |  |  | 505 |  |  |  |  | 510 |  |  |

| aaa | gga | cta | ttc | tgc | cct | aga | cgt | ggg | agt | agg | gtt | gag | gga | tgg | aac | 1644 |
| Lys | Gly | Leu | Phe | Cys | Pro | Arg | Arg | Gly | Ser | Arg | Val | Glu | Gly | Trp | Asn |
|  |  | 515 |  |  |  |  | 520 |  |  |  |  | 525 |  |  |  |

| caa | gga | gaa | ggg | ggc | tgt | taggctggaa | gcagtaacga | ggaagaataa |  |  |  |  |  |  |  | 1692 |

```
Gln Gly Glu Gly Gly Cys
    530 tgaagagagg gcttgctggg agtcctcaga ctcctctcct aacccacccc ttcctttcca    1752 gtggcagagg gcaaagtgtg tgacccactg tgctcctctg ggggatgctg gggcccaggc    1812 cctggtcagt gcttgtcctg tcgaaattat agccgaggag gtgtctgtgt gacccactgc    1872 aactttctga atgggtacag taaggggagc cagtcaagga tgggtggggg tggggccctg    1932 caatggaact gttcaggtgg catacaataa aagtctttag acagcaaaaa aaaaaaaaaa    1992 aaaaaaaaaa aaa                                                       2005

<210> SEQ ID NO 6
<211> LENGTH: 534
<212> TYPE: PRT
<213> ORGANISM: Homo sapiens

<400> SEQUENCE: 6

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300
```

-continued

```
Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
            405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Gly Glu Gly
            485                 490                 495

Lys Gly Leu Leu Gly Gly Glu Asn Arg Glu Ser Gly Arg Arg Gly Leu
            500                 505                 510

Lys Gly Leu Phe Cys Pro Arg Arg Gly Ser Arg Val Glu Gly Trp Asn
        515                 520                 525

Gln Gly Glu Gly Gly Cys
    530

<210> SEQ ID NO 7
<211> LENGTH: 1320
<212> TYPE: DNA
<213> ORGANISM: Homo sapiens
<220> FEATURE:
<221> NAME/KEY: CDS
<222> LOCATION: (61)..(1260)

<400> SEQUENCE: 7
cgggcccccc ctcgaggtcg ggccggactt ggctgggctc ccttcaccct ctgcggagtc      60 atg agg gcg aac gac gct ctg cag gtg ctg ggc ttg ctt ttc agc ctg     108
Met Arg Ala Asn Asp Ala Leu Gln Val Leu Gly Leu Leu Phe Ser Leu
1               5                  10                  15 gcc cgg ggc tcc gag gtg ggc aac tct cag gca gtg tgt cct ggg act     156
Ala Arg Gly Ser Glu Val Gly Asn Ser Gln Ala Val Cys Pro Gly Thr
            20                  25                  30 ctg aat ggc ctg agt gtg acc ggc gat gct gag aac caa tac cag aca     204
Leu Asn Gly Leu Ser Val Thr Gly Asp Ala Glu Asn Gln Tyr Gln Thr
        35                  40                  45 ctg tac aag ctc tac gag agg tgt gag gtg gtg atg ggg aac ctt gag     252
Leu Tyr Lys Leu Tyr Glu Arg Cys Glu Val Val Met Gly Asn Leu Glu
    50                  55                  60 att gtg ctc acg gga cac aat gcc gac ctc tcc ttc ctg cag tgg att     300
Ile Val Leu Thr Gly His Asn Ala Asp Leu Ser Phe Leu Gln Trp Ile
65                  70                  75                  80
```

```
cga gaa gtg aca ggc tat gtc ctc gtg gcc atg aat gaa ttc tct act    348
Arg Glu Val Thr Gly Tyr Val Leu Val Ala Met Asn Glu Phe Ser Thr
             85                  90                  95 cta cca ttg ccc aac ctc cgc gtg gtg cga ggg acc cag gtc tac gat    396
Leu Pro Leu Pro Asn Leu Arg Val Val Arg Gly Thr Gln Val Tyr Asp
        100                 105                 110 ggg aag ttt gcc atc ttc gtc atg ttg aac tat aac acc aac tcc agc    444
Gly Lys Phe Ala Ile Phe Val Met Leu Asn Tyr Asn Thr Asn Ser Ser
    115                 120                 125 cac gct ctg cgc cag ctc cgc ttg act cag ctc acc gag att ctg tca    492
His Ala Leu Arg Gln Leu Arg Leu Thr Gln Leu Thr Glu Ile Leu Ser
130                 135                 140 ggg ggt gtt tat att gag aag aac gat aag ctt tgt cac atg gac aca    540
Gly Gly Val Tyr Ile Glu Lys Asn Asp Lys Leu Cys His Met Asp Thr
145                 150                 155                 160 att gac tgg agg gac atc gtg agg gac cga gat gct gag ata gtg gtg    588
Ile Asp Trp Arg Asp Ile Val Arg Asp Arg Asp Ala Glu Ile Val Val
                165                 170                 175 aag gac aat ggc aga agc tgt ccc ccc tgt cat gag gtt tgc aag ggg    636
Lys Asp Asn Gly Arg Ser Cys Pro Pro Cys His Glu Val Cys Lys Gly
            180                 185                 190 cga tgc tgg ggt cct gga tca gaa gac tgc cag aca ttg acc aag acc    684
Arg Cys Trp Gly Pro Gly Ser Glu Asp Cys Gln Thr Leu Thr Lys Thr
        195                 200                 205 atc tgt gct cct cag tgt aat ggt cac tgc ttt ggg ccc aac ccc aac    732
Ile Cys Ala Pro Gln Cys Asn Gly His Cys Phe Gly Pro Asn Pro Asn
    210                 215                 220 cag tgc tgc cat gat gag tgt gcc ggg ggc tgc tca ggc cct cag gac    780
Gln Cys Cys His Asp Glu Cys Ala Gly Gly Cys Ser Gly Pro Gln Asp
225                 230                 235                 240 aca gac tgc ttt gcc tgc cgg cac ttc aat gac agt gga gcc tgt gta    828
Thr Asp Cys Phe Ala Cys Arg His Phe Asn Asp Ser Gly Ala Cys Val
                245                 250                 255 cct cgc tgt cca cag cct ctt gtc tac aac aag cta act ttc cag ctg    876
Pro Arg Cys Pro Gln Pro Leu Val Tyr Asn Lys Leu Thr Phe Gln Leu
            260                 265                 270 gaa ccc aat ccc cac acc aag tat cag tat gga gga gtt tgt gta gcc    924
Glu Pro Asn Pro His Thr Lys Tyr Gln Tyr Gly Gly Val Cys Val Ala
        275                 280                 285 agc tgt ccc cat aac ttt gtg gtg gat caa aca tcc tgt gtc agg gcc    972
Ser Cys Pro His Asn Phe Val Val Asp Gln Thr Ser Cys Val Arg Ala
    290                 295                 300 tgt cct cct gac aag atg gaa gta gat aaa aat ggg ctc aag atg tgt   1020
Cys Pro Pro Asp Lys Met Glu Val Asp Lys Asn Gly Leu Lys Met Cys
305                 310                 315                 320 gag cct tgt ggg gga cta tgt ccc aaa gcc tgt gag gga aca ggc tct   1068
Glu Pro Cys Gly Gly Leu Cys Pro Lys Ala Cys Glu Gly Thr Gly Ser
                325                 330                 335 ggg agc cgc ttc cag act gtg gac tcg agc aac att gat gga ttt gtg   1116
Gly Ser Arg Phe Gln Thr Val Asp Ser Ser Asn Ile Asp Gly Phe Val
            340                 345                 350 aac tgc acc aag atc ctg ggc aac ctg gac ttt ctg atc acc ggc ctc   1164
Asn Cys Thr Lys Ile Leu Gly Asn Leu Asp Phe Leu Ile Thr Gly Leu
        355                 360                 365 aat ggg tta gag atc ctg cct tcc ctc ctt aga ccc cag ccc acg cac   1212
Asn Gly Leu Glu Ile Leu Pro Ser Leu Leu Arg Pro Gln Pro Thr His
    370                 375                 380 ccc tca cag ttc att tca ttg gcc aaa act ttc cta tgt gga gct gac   1260
Pro Ser Gln Phe Ile Ser Leu Ala Lys Thr Phe Leu Cys Gly Ala Asp
385                 390                 395                 400
```
taggaatcaa agtcataaaa ttctagcctg ttaaaaaaaa aaaaaaaaaa aaaaaaaaaa    1320

<210> SEQ ID NO 8
<211> LENGTH: 400
<212> TYPE: PRT
<213> ORGANISM: Homo sapiens

<400> SEQUENCE: 8

```
Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365
```

-continued

```
Asn Gly Leu Glu Ile Leu Pro Ser Leu Leu Arg Pro Gln Pro Thr His
    370                 375                 380

Pro Ser Gln Phe Ile Ser Leu Ala Lys Thr Phe Leu Cys Gly Ala Asp
385                 390                 395                 400
```